US005441048A

United States Patent [19]

Schoendorfer

[11] Patent Number: 5,441,048
[45] Date of Patent: Aug. 15, 1995

[54] METHOD AND APPARATUS FOR DETERMINATION OF CHEMICAL SPECIES IN PERSPIRATION

[75] Inventor: Donald W. Schoendorfer, Santa Ana, Calif.

[73] Assignee: Sudor Partners, Santa Ana, Calif.

[21] Appl. No.: 989,204

[22] Filed: Dec. 11, 1992

Related U.S. Application Data

[63] Continuation-in-part of Ser. No. 569,007, Aug. 15, 1990, Pat. No. 5,203,327, which is a continuation-in-part of Ser. No. 241,707, Sep. 8, 1988, Pat. No. 4,957,108.

[51] Int. Cl.$^6$ ................................................ A61B 5/00
[52] U.S. Cl. .................................... 128/632; 128/636; 128/760; 128/771
[58] Field of Search ............... 128/632, 636, 637, 760, 128/771; 604/312

[56] References Cited

U.S. PATENT DOCUMENTS

| 3,552,929 | 1/1971 | Fields et al. . |
| 4,190,060 | 2/1980 | Greenleaf et al. . |
| 4,287,153 | 9/1981 | Townsend . |
| 4,329,999 | 5/1982 | Phillips . |
| 4,341,207 | 7/1982 | Steer et al. . |
| 4,360,015 | 11/1982 | Mayer . |
| 4,444,193 | 4/1984 | Fogt et al. . |
| 4,542,751 | 9/1985 | Webster et al. . |
| 4,595,011 | 6/1986 | Phillips . |
| 4,631,174 | 12/1986 | Kondo . |
| 4,667,665 | 5/1987 | Blanco et al. . |
| 4,706,676 | 11/1987 | Peck . |
| 4,732,153 | 3/1988 | Phillips . |
| 4,756,314 | 7/1988 | Eckenhoff et al. . |
| 4,821,733 | 4/1989 | Peck . |
| 4,909,256 | 3/1990 | Peck . |
| 4,957,108 | 9/1990 | Schoendorfer et al. . |
| 4,960,467 | 10/1990 | Peck . |
| 5,094,248 | 3/1992 | Kawam . |
| 5,113,860 | 5/1992 | McQuinn .................... 128/632 |

FOREIGN PATENT DOCUMENTS

| 0099748 | 2/1984 | European Pat. Off. . |
| 0217403 | 4/1987 | European Pat. Off. . |
| 2157955 | 11/1985 | United Kingdom . |
| WO8904630 | 6/1989 | WIPO . |

OTHER PUBLICATIONS

Abuscreen Radioimmunoassay for Cocaine Metabolite, Product Insert, Roche Diagnostic Systems, Inc., Nov., 1987, Nutley, N.J. (numbers of relevant pages and author unknown).
Coat-A-Count Cocaine Metabolite, Product Insert, DPC Diagnostic Products Corporation, May 11, 1989, Los Angeles, pp. 1-13 (author unknown).
Weast, Robert C., ed., Handbook of Chemistry and Physics, 47th ed., 1966, p. C-247 (author unknown).
Jackson, et al., Clinical Chemistry, vol. 30, No. 7, 1984, pp. 1157-1162, "Two-site monoclonal antibody assays for human heart-and brain-type creatine kinase".
Howard, Michael J, et al., ed., *Films, Sheets, and Laminates, a desk-top data bank*, The International Plastics Selector, Inc., San Diego, Calif., pp. xli, B-269, B-296, B-358, B-524, B-893 (no author listed).

*Primary Examiner*—Lee S. Cohen
*Attorney, Agent, or Firm*—Knobbe, Martens, Olson & Bear

[57] ABSTRACT

A dermal patch to be worn on the skin for increasing the concentration of an analyte expressed through the skin in perspiration to a conveniently measurable level. Included are patches and methods of using such patches to determine the quantity of an analyte in a given volume of perspiration, to determine a subject's sensitivity to an allergen, to allow an analyte to be detected with conventional detection systems, and to dissolve the structural components of a patch to facilitate analyte detection.

29 Claims, 5 Drawing Sheets

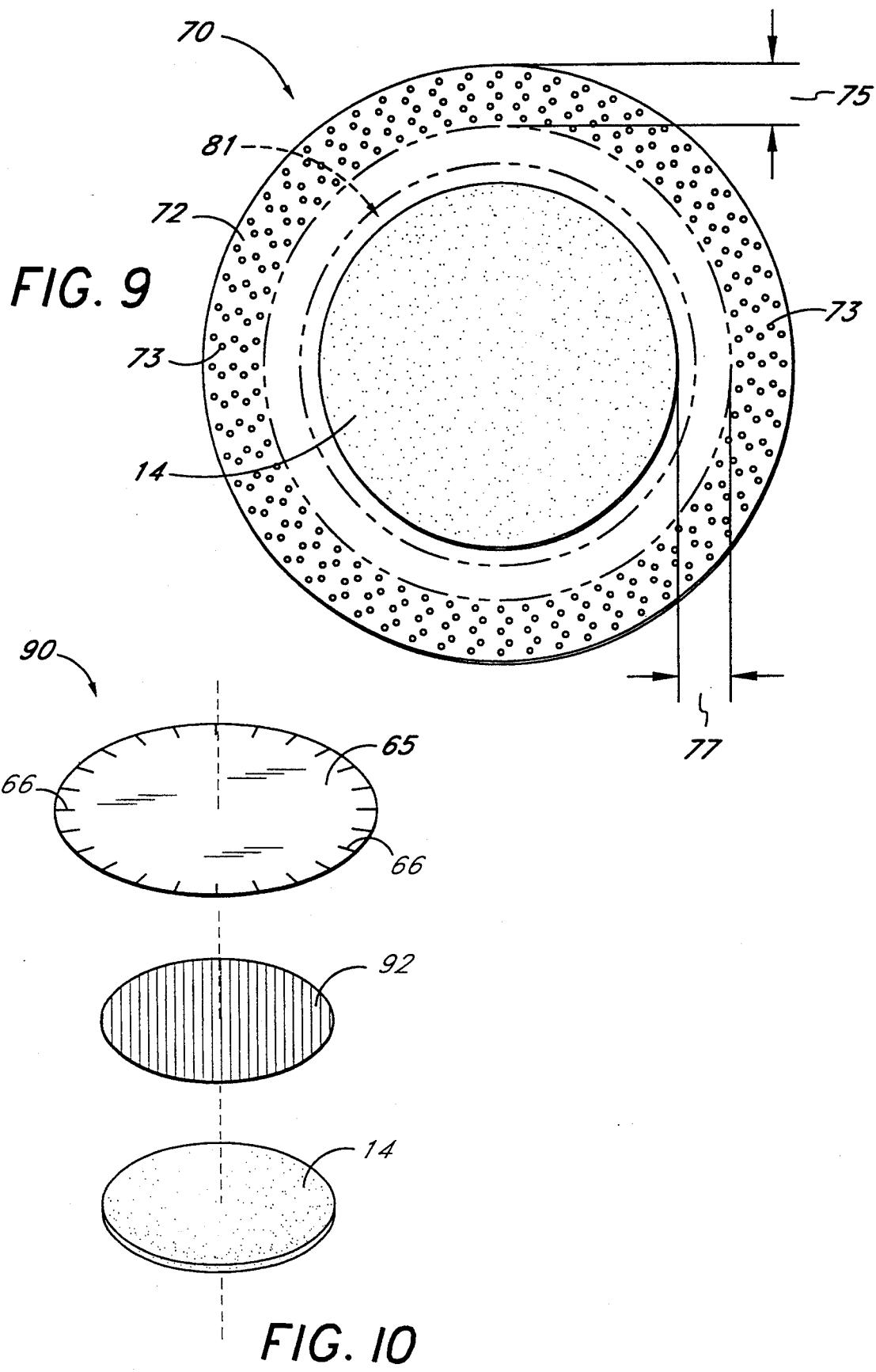

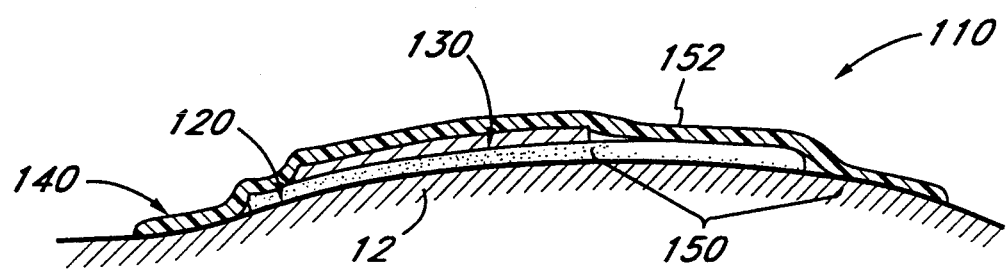
FIG. II

METHOD AND APPARATUS FOR DETERMINATION OF CHEMICAL SPECIES IN PERSPIRATION

This is a continuation-in-part of a continuation-in-part application Ser. No. 569,007, filed Aug. 15, 1990, now U.S. Pat No. 5,203,327, inventors Donald W. Schoendorfer and William R. Miller, which is a continuation-in-part of parent patent application Ser. No. 241,707, filed Sep. 8, 1988, now U.S. Pat. No. 4,957,108, inventors Donald W. Schoendorfer and William R. Miller, entitled Method and Apparatus for Determination of Chemical Species in Body Fluid.

FIELD OF THE INVENTION

The present invention relates to dermal patches for accumulating an analyte expressed through the skin in perspiration and to methods of using such patches.

BACKGROUND OF THE INVENTION

A. Chemical Analysis of Body Fluids

The determination of a patient's physiological status is frequently assisted by a chemical analysis of a body fluid of that patient. Such an analysis normally determines the existence and/or concentration of a chemical species in the body fluid of the patient as an indication of that patient's condition. Increasingly, such analyses are being used to determine the presence of a drug of addiction or a metabolite of such a drug in the body fluid of an individual.

Many analytes of interest can be detected in urine, which is readily available from a subject and can be collected non-invasively. For these reasons, the primary method for detecting drugs of abuse today is urine analysis.

Blood, however, is also frequently analyzed for the presence of drugs of addiction as well as a wide variety of other analytes. Blood collection is, however, inherently invasive, and carries the risk of infection associated with any invasive procedure. Blood testing must also be conducted at a physician's office or at another facility equipped to analyze blood, which reduces the convenience of blood tests and increases their cost. In addition, testing a blood sample can only reveal information about chemicals or metabolites that are present in the blood of the subject at the time the sample is taken, and cannot detect the presence of such analytes over a period of time.

Perspiration can also be collected in order to analyze a chemical species present in the body. The non-invasive manner in which it can be collected renders perspiration suitable for use outside of a physician's office. In addition, a variety of molecules which are expressed in perspiration can be analyzed.

B. Diagnostic Kits for Collecting Perspiration

A variety of diagnostic kits for monitoring an analyte in sweat have been developed. For example, U.S. Pat. No. 3,552,929 to Fields, et al. discloses a band-aid-type test patch suited for determining the chloride ion concentration in perspiration as a method of diagnosing cystic fibrosis. The apparatus disclosed in Fields comprises an absorptive sweat collecting pad with an impermeable overlying layer for the purpose of preventing evaporation. When the absorptive pad is saturated, the patch is removed from the skin and exposed to a series of strips impregnated with incremental quantities of silver chromate or silver nitrate, the color of which undergoes a well known change upon conversion to the chloride salt.

U.S. Pat. No. 4,706,676 to Peck discloses a dermal collection device which comprises a binder to prevent reverse migration of an analyte, a liquid transfer medium which permits transfer of an analyte from the dermal surface to the binder, and an occlusive cover across the top of the liquid transfer medium and binder. Peck also discloses the application of such a dermal collection patch to detect various environmental chemicals to which humans are exposed. After the dermal collection device has been worn on a patient's skin for a period of time, the patch is removed for analysis, which involves the chemical separation of the bound substance of interest from the binding reservoir and thereafter undertaking qualitative and/or quantitative measurement of the substance of interest by conventional laboratory techniques.

Another quantitative sweat collection patch is disclosed in U.S. Pat. No. 4,756,314 to Eckenhoff. This patch uses a diffusion rate-limited membrane as a means to maintain a constant flow of fluid into the patch. The patch comprises an impermeable outer boundary structure, and is therefore an occlusive patch.

However, prior art diagnostic test patches are generally only useful for determining the presence of analytes which are present in sweat in relatively high concentrations, such as halide ions. In addition, the occlusive outer layer-type devices of the prior art are susceptible to the problem of back diffusion of perspiration and/or the analytes contained therein, including changes in the skin's transport characteristics, both outward (Brebner, D. F., J. Physiol, 175: 295–302 (1964)) and inward (Feldmann, R. J., Arch. Dermat., 91: 61–666 (1965)). The maintenance of this aqueous state also fosters bacterial colonization. Thus, there remains a need in many diverse applications for an improved method and apparatus for the non-invasive determination of the presence or concentration of an analyte in a body fluid such as perspiration.

SUMMARY OF THE INVENTION

In one aspect, the present invention comprises a dermal patch to be worn on the skin of a subject mammal for quantitatively determining the presence and amount of an analyte in that subject's perspiration. This dermal patch includes:

a fluid permeable support layer in fluid communication with the subject's skin when the patch is worn on the subject's skin, wherein the support layer comprises a rate-limited structure that limits the rate of diffusion of perspiration through the support layer; and an absorbent material in fluid communication with the support layer for collecting non-aqueous components of perspiration which diffuse through the support layer, the support layer being located between the absorbent material and the subject's skin when the patch is worn on the subject's skin.

In a preferred embodiment, a gas permeable layer is located between the absorbent material and the outside of the patch, wherein water and other fluids expressed through the skin of the subject are permitted to escape through the gas permeable layer in their vapor phase to the outside of the patch. In order to attach a patch to the skin of a subject according to this aspect of the present invention, the gas permeable layer can further include an adhesive composition applied to the outer perimeter of the outer protective layer on the side of the outer protective layer in contact with the skin of the subject. The gas permeable layer can also be used to form a pooling area between the gas permeable layer and the subject's skin when the patch is worn on the subject's skin. Such a pooling area is used to collect excess perspiration that is not diffused across the support layer. In one embodiment, the absorbent material is in fluid communication with the pooling area only through the support layer.

The absorbent material in this aspect of the present invention can be made from various materials, including paper or cotton gauze. In one embodiment, the collection of an analyte of interest from the perspiration of the subject in the absorbent material is improved by providing the absorbent material with a specific binding partner for the analyte. For example, the binding partner can be an antibody. In another preferred embodiment, the absorbent material of the patch can be dissolved into a solution such that the dissolved material and solution do not interfere with the analysis of the analyte to be detected.

The rate-limited structure of the patch is advantageously a membrane, such as a polycarbonate microporous membrane or a membrane made from nylon 6/6. In a preferred embodiment, the rate-limited structure limits the rate of diffusion of perspiration across the support layer to less than the insensible rate of perspiration through the skin of the subject.

In another aspect of the present invention, a dermal patch to be worn on the skin of a subject mammal for determining the presence of an analyte in the subject's perspiration is disclosed, wherein the patch comprises an absorbent material in fluid communication with the skin of the subject for collecting non-aqueous components of perspiration which diffuse through the skin of the subject, and wherein the absorbent material can be dissolved into a solution such that the dissolved absorbent material and solution do not interfere with the analysis of the components of perspiration. The absorbent material in this aspect of the present invention can be made from any of a number of dissolvable materials, including protein, nylon 6/6, phenolic, polyurethane (TP), and polyester (PBT). Likewise, a number of solvents for dissolving such absorbent materials can be used, including acids and bases, the particular solvent depending on the material to be dissolved. For example, if the absorbent material is polystyrene, the solvent can be selected from the group consisting of chlorinated hydrocarbons, aromatic hydrocarbons, esters, ketones, essential oils of high terpene content, and turpentine. Examples of these solvents are cyclohexanone, dichloroethylene, and methylenedichloride. The absorbent material can also be provided with a specific binding partner for an analyte present in the perspiration of the subject. In one embodiment, the non-aqueous components of perspiration to be detected include a drug of abuse such as cocaine.

In another embodiment, a patch according to this aspect of the present invention can be provided with an allergenic material placed in fluid communication with the skin of the subject. Such a patch can be used to determine whether a subject is allergic to that particular allergen. The patch in this aspect can additionally comprise a fluid permeable support layer in fluid communication with the subject's skin and located between the absorbent material and the subject's skin. The support layer, in one embodiment, can further comprise a rate-limited structure between the absorbent material and the skin, wherein the structure allows the passage of perspiration through the structure but at a rate lower than the insensible rate of perspiration through the skin of the subject. The rate-limited structure can also comprise a separate layer of material.

The patch in this aspect of the invention can additionally comprise a gas permeable outer protective layer located between the absorbent material and the outside of the patch. This layer can, in one embodiment, further define a pooling area between the outer protective layer and the skin of the subject when the patch is on the subject's skin, the absorbent material being in fluid communication with the pooling area only through the rate-limited structure.

In yet another aspect of the present invention, a dermal patch to be worn on the skin of a subject mammal is disclosed which can be used to determine the sensitivity of the subject to an allergen. Such a patch comprises:
an absorbent material in fluid communication with the skin of the subject for collecting non-aqueous components of perspiration which diffuse through the skin of the subject; and
an allergen located proximate to the patch which is in fluid communication with the subject's skin when the patch is worn on the subject's skin.

In a preferred embodiment, the patch further comprises a gas permeable layer located between the absorbent material and the outside of the patch, wherein water and other fluids expressed through the skin of the subject are permitted to escape through the gas permeable layer in their vapor phase to the outside of the patch. This patch can additionally comprise a support layer in fluid communication with the skin of the subject, the support layer being located between the absorbent material and the skin of the subject when the patch is worn on the subject's skin. An agent for increasing the permeability of capillaries in the dermis immediately beneath the patch can be placed in fluid communication with the subject's skin when the patch is worn on the subject's skin, for example in the support layer or in the absorbent material.

In one embodiment of this aspect of the present invention, the absorbent material can be dissolved into a solution such that the dissolved material and solution do not interfere with the analysis of the desired body components. The absorbent material can also contain a specific binding partner for the desired body components indicative of sensitivity to an allergen. Such a specific binding partner can be, for example, an antibody or an antigen. This aspect of the invention can additionally comprise an outer protective layer, which advantageously includes an adhesive composition applied to the outer perimeter of the outer protective layer on the side of the outer protective layer which contacts the skin of the subject, in order to attach the patch to the skin of the subject. This embodiment can also comprise a rate-limited structure between the absorbent material and the skin of the subject when the patch is worn on the skin of the subject, as well as a pooling area between the outer protective layer and the skin of the subject when the patch is on the subject's skin, the absorbent material being in fluid communication with the pooling area only through the rate-limited structure.

In a further aspect of the present invention, a method of quantitatively determining the presence of an analyte contained in the perspiration of a subject mammal is disclosed, comprising the steps of:

a. placing a patch on the skin of a mammal, wherein the patch comprises an absorbent material capable of concentrating non-aqueous components of the perspiration of the mammal;

b. passing perspiration of the mammal through a rate-limited structure at a known rate to the absorbent material, the structure being positioned between the skin of the mammal and the absorbent material when the patch is worn on the skin of the mammal, the structure being of a known area;

c. removing the patch after a sufficient test period of time has elapsed so that the analyte can be detected by an assay for the analyte;

d. recording the amount of time the patch was worn in order to determine the total amount of perspiration which passed across the structure;

e. determining the amount of an analyte contained in the patch; and f. relating the amount of analyte determined in step (e) to the amount of perspiration determined in step (d) in order to determine the average amount of the analyte in the mammal's perspiration.

The rate-limited structure in this aspect of the invention can advantageously be either a polycarbonate microporous membrane or a membrane made from nylon 6/6. The absorbent material, in one embodiment, can also be paper. The absorbent material in this aspect can also advantageously have attached thereto a binding partner for a specific analyte. For example, the binding partner can be an antibody or an antigen. In yet a further aspect of the present invention, a method of detecting metabolites of an analyte contained in the perspiration of a subject mammal is disclosed, the method comprising:

a) passing an analyte through the skin of the mammal in the perspiration of the mammal;

b) collecting the analyte in an absorbent material;

c) chemically modifying the analyte after the analyte has been collected on the absorbent material; and d) detecting the analyte.

In a preferred embodiment, this method can additionally comprise the step of freeing the analyte from the absorbent material after the analyte has been collected on the absorbent material. In this embodiment, the freeing step can comprise eluting the analyte from the absorbent material with a solvent. The freeing step can also comprise dissolving the absorbent material into a solution with a solvent such that the dissolved material and solution do not interfere with the detection of the analyte, where the absorbent material comprises a dissolvable material. In another preferred embodiment, the step of chemically modifying the analyte comprises exposing the analyte to a solution having an alkaline pH. This method can also further comprise heating the analyte during the step of chemically modifying it. In yet another embodiment, this step can comprise incubating the analyte with an enzyme capable of hydrolyzing the analyte. In all of the foregoing embodiments, any of a number of analytes can be detected, such as cocaine.

A further aspect of the present invention is a method of determining whether a subject mammal is allergic to a particular allergen. This method comprises:

placing a patch on the surface of the skin of the mammal, wherein the patch comprises an absorbent material in fluid communication with the skin of the mammal when the patch is worn on the skin of the mammal, the absorbent material including the allergen;

inducing the migration to the absorbent material of components of the body of the mammal associated with an allergic reaction to the allergen; and detecting the components to determine whether the mammal has expressed an allergic response to the allergen.

In one embodiment of this aspect of the present invention, the absorbent material additionally comprises a composition for increasing the permeability of capillaries in the dermis immediately beneath the patch. In yet another aspect of the present invention, a method for determining whether a subject mammal is allergic to a particular allergen is disclosed which comprises the steps of:

exposing the skin of the mammal to the allergen;

accumulating perspiration from the mammal proximate to the area of the skin of the mammal exposed to the allergen; and detecting the presence of an analyte in the perspiration, wherein the analyte is indicative of an allergic reaction to the allergen.

In one embodiment, this method further comprises applying a composition to the skin of the mammal that increases capillary permeability.

Another aspect of the present invention comprises a method for determining the presence of an analyte in the perspiration of a subject mammal, comprising the steps of:

accumulating perspiration containing an analyte from the subject on an absorbent material, wherein the absorbent material can be dissolved by a solvent into a solution;

dissolving the absorbent material containing the analyte with a solvent, wherein the solvent does not interfere with the detection of the analyte;

detecting the analyte in the solution.

In one embodiment, the detecting step additionally comprises chemically modifying the analyte and detecting a metabolite of the analyte in order to detect the presence of the analyte. In a preferred embodiment, the absorbent material is a material selected from the group consisting of protein, nylon 6/6, phenolic, polyurethane (TP), and polyester (PBT). In this embodiment, the solvent is preferably selected from the group consisting of an acid and a base. In a further embodiment, the absorbent material is polystyrene and the solvent is selected from the group consisting of chlorinated hydrocarbons, aromatic hydrocarbons, esters, ketones, essential oils of high terpene content, and turpentine. For example, the solvent can be cyclohexanone, dichloroethylene, or methylenedichloride.

BRIEF DESCRIPTION OF THE DRAWINGS

FIG. 9 is a plan view of a dermal patch according to a further embodiment of the present invention.

FIG. 10 is an exploded elevational view according to still another embodiment of the present invention.

FIG. 11 is a cross-sectional view of a dermal patch of the present invention which includes a pooling area.

DETAILED DESCRIPTION OF THE PREFERRED EMBODIMENTS

I. Dermal Patches for Detecting Analytes

A. Non-Occlusive Dermal Patches

Figure 1:
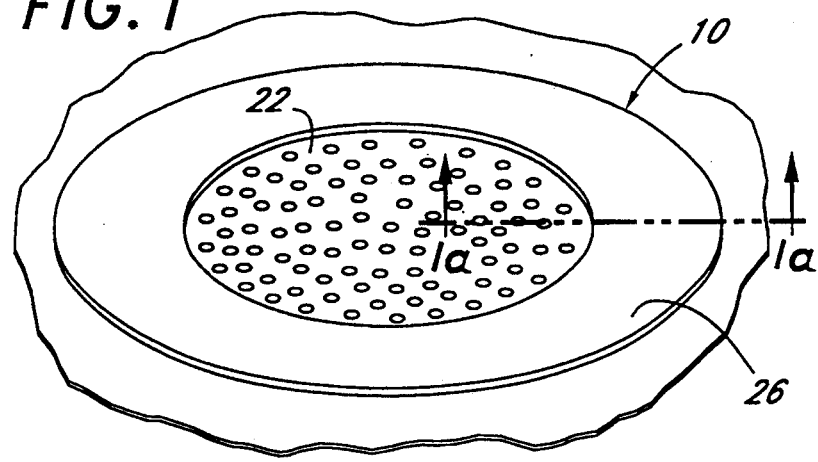
FIG. 1 is a perspective view of a dermal patch according to one embodiment of the present invention.

Referring to FIG. 1, there is disclosed a dermal patch 10 according to one embodiment of the present invention, illustrated as being secured to the surface of the skin 12 of a subject. As will be appreciated by one of skill in the art, the patch of the present invention may be used for veterinary purposes as well as on humans. In addition, the patch can be used in more diverse applications such as in agriculture or any other environment where a chemical species is to be detected in a fluid. The preferred use, however, is for determination of preselected chemical species or analyte in sweat (perspiration), and the ensuing discussion is principally directed to that use.

Moisture expressed from the skin 12 within the perimeter of the test patch 10 first accumulates in a concentration zone 14 beneath the first side of a gas permeable filter or layer 16 which is in fluid communication with the skin 12. The concentration zone 14 preferably contains an absorbent material, such as a fluid permeable medium 20 which may be cotton gauze or other commonly available fluid permeable material. For example, a layer of any of a variety of known fiber webs such as knitted fabrics, or non-woven rayon or cellulose fibers may be used. Filtration Sciences #39 is a particularly preferred fluid-permeable medium for use as a concentration zone in the present invention. In a preferred embodiment, the absorbent material contains binders, such as antibodies, for specifically binding analytes of interest to the absorbent material of the patch. As used herein, the term "absorbent material" designates any fluid permeable material capable of collecting or holding analytes contained in perspiration. Preferably, such a material is also able to concentrate such analytes on the patch.

The term "fluid permeable" is used herein to describe a material which will permit the passage of the liquid phase of fluids expressed from the skin and which will also allow the passage of the vapor phase of such fluids. A fluid permeable filter or layer will thus allow the passage of water in both the liquid and vapor phases. "Water" is used herein to denote both the liquid and vapor phases of water unless reference is specifically made to a particular phase.

Moisture from perspiration accumulates in the interfiber spaces of the medium 20. Under the influence of body heat which is readily conducted from the surface of the skin through the liquid phase, the liquid water component of the perspiration will tend to volatilize. Such volatilized water can thereby pass through the gas permeable filter or layer 16, which is located on the side of the medium 20 distal of the skin 12, and leave the patch 10.

As previously discussed, the patch 10 is provided with a gas permeable filter 16. The term "gas permeable" is used to describe a material which permits the passage of gases, including the vapor phase of fluids expressed from the skin, but substantially retains the fluid phase within the patch. Any of a variety of suitable commercially available microfiltration membrane filters may be used for this purpose, such as the Gore-Tex 0.45 micron Teflon filter manufactured by W. L. Gore & Associates, Inc. (Elkton, Md.).

Adjacent a second side of the gas permeable filter 16 is a discharge zone 18. As previously discussed, the gas permeable filter 16 retains the fluid phase but permits escape of the vapor phase of the fluid component in perspiration. Thus, the vapor component, which primarily consists of vaporized water, continuously escapes through the gas permeable filter 16 exiting the second side thereof into discharge zone 18, which is in communication with the atmosphere. In an alternative embodiment, not separately illustrated, the gas permeable filter 16 is replaced by a fluid permeable membrane which permits passage of the liquid phase. In this embodiment, liquid, or a combination of vapor and liquid, will be permitted to escape from the patch. Any of a variety of fluid permeable filters are commercially available which can be used to form a fluid permeable filter used in this embodiment of the present invention. A preferred fluid permeable filter is constructed from James River Paper Drape.

A flexible, gas permeable outer layer 22 is preferably disposed adjacent the second side of filter 16 in the discharge zone 18. This layer serves to protect the filter 16 against physical damage such as abrasion, and can also serve as a barrier for preventing chemical contamination of the filter material from the outside. Outer layer 22 may comprise any of a variety of commercially available gas permeable tapes and films which are known to one of skill in the art. Outer layer 22 may also be distinct from or integral with tape 26, discussed below. Alternatively, depending upon the intended application of the patch, outer layer 22 may be deleted altogether, where it does not appear that abrasion or external contamination will deleteriously affect the patch 10, or where the gas permeable layer 16 is made from a material which is itself resistant to abrasion and/or external contamination, thus obviating the need for the outer layer 22.

The patch 10 illustrated in FIG. 1 is secured to the surface of the skin by means of a peripheral band of tape 26. Preferably, the tape 26 will extend around all sides of the patch 10. For example, an annular ring of tape can be die punched for use with a circular patch, or the center of a rectangular piece of tape can be removed to expose outer layer 22 or filter 16 of a rectangular patch (see FIGS. 1 and 3, respectively). Alternatively, outer layer 22 and tape 26 can be deleted altogether and layers 16 and 20 can be secured to the surface of the skin by a bandage or through the use of an adhesive. One such method would be to capture layers 16 and 20 under a bandage or wrapping surrounding the arm or the leg. In this case, the gases and/or fluids are permitted to escape through layers 16 and 20 and into the bandage, where they may either collect or from which they are dissipated into the environment.

A large variety of hypoallergenic or other suitable tapes are well known in the art, which may be adapted for use with the patch 10 of the present invention. Different tapes or adhesives may be desirable depending upon the intended use of the test kit, based upon their ability to adhere to the skin during different conditions such as daytime wearing under clothing, during sleep, during profuse sweating for prolonged periods or during showers. It has been determined that the most desirable tapes include multiple perforations which prevent sweat from building up underneath the tape and eventually compromising the integrity of the adhesive. Preferably, a tape, such as Dermiclear marketed by Johnson & Johnson, is used. More preferably, the tape comprises a layer of 3M 1625 Tegaderm wound dressing available from the 3M Company (St. Paul, Minn.).

Any of a wide variety of means for securing the patch 10 to the skin 12 may be utilized. For example, the tape 26 can be eliminated and gauze layer 20 provided with a lower adhesive layer to perform the same function. One such adhesive membrane is the MN-100 adhesive membrane manufactured by Memtec of Minnetonka, Minn. This membrane is fluid permeable so that it passes fluid as would the gauze layer 20, yet has one adhesive side so that it will stick to the skin. Alternatively, outer protective layer 22 can comprise an annular flange 23, extending radially outwardly beyond the outer edges of filter 16 and gauze 20 (see FIG. 2a). The lower surface of the flange 23 is then provided with a suitable adhesive.

The surface temperature of human skin varies regionally. However, it is generally within the range of from about 86° F. to about 90° F. at rest, and can rise to much higher temperatures under conditions of strenuous exertion. At those temperatures, a number of chemical species of interest for the purpose of the present invention, such as creatine kinase or a high or low density lipoprotein, have a sufficiently low vapor pressure that volatilization is not a significant factor in the efficiency of the concentration function. At the same time, the substantial aqueous component will have a sufficiently high vapor pressure that it will tend to volatilize, thereby concentrating the less volatile fractions. However, in some applications the chemical species of interest will have a high enough vapor pressure, even at the resting temperature of human skin or the temperature of another surface to which a patch of the present invention is applied, such that escape of the vapor phase through the gas permeable filter 16 of the analyte of interest will disadvantageously impair the efficacy of the test patch. For these analytes, a modified patch must be used.

B. Dermal Patches for Detecting Volatile Analytes

Figure 2:
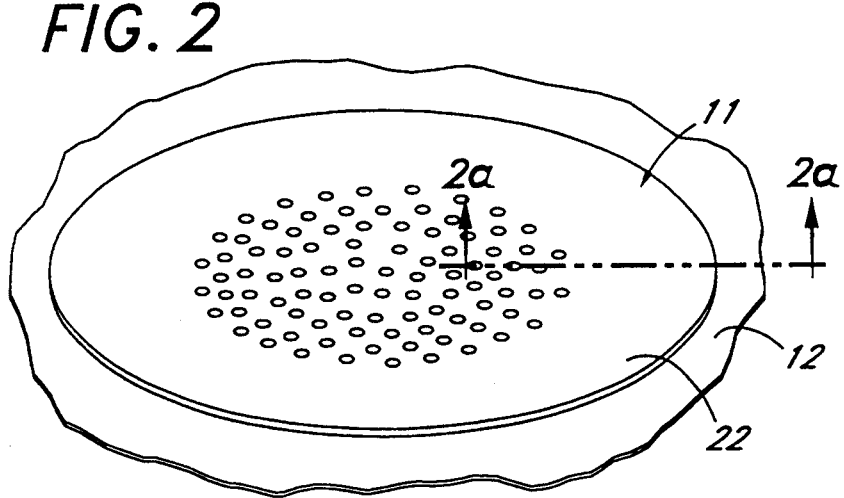
FIG. 2 is a perspective view of a dermal patch according to a second embodiment of the present invention.
Figure 2A:
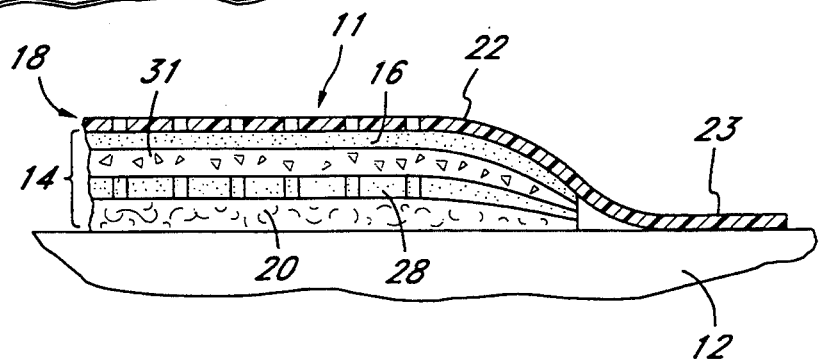
FIG. 2a is a cross-sectional view along the line 2a—2a of the dermal patch of FIG. 2.

Referring to FIGS. 2 and 2a, there is disclosed a modified patch 11 according to the present invention for use in detecting an analyte having a propensity to escape through the gas permeable filter 16 as a vapor under ordinary use conditions. The test patch 11 comprises a concentration zone 14 defined on its inner boundary by the skin 12 to which the patch 11 is secured. The outer boundary of the concentration zone 14 is defined by the gas permeable filter or layer 16, which separates the concentration zone 14 from the discharge zone 18. Disposed in the concentration zone 14, and adjacent the gas permeable filter 16, is a binder layer 31 for binding and preventing the escape of molecules of the volatile analyte. The binder layer 31 is separated from the gauze layer 20 by a porous layer 28, which may compromise any of a variety of films for retaining the binder layer 31 yet permitting passage of fluid.

In the embodiment illustrated in FIG. 2a, perspiration will pool in the interfiber spaces of the gauze 20, and will percolate through porous layer 28 into the binder layer 31. In that layer, a chemically active or biochemically active binder material will act to selectively bind the volatile analyte, thereby preventing it from escaping as a vapor through gas permeable filter 16. As discussed in connection with the embodiment illustrated in FIG. 1, it is also possible to replace the gas permeable filter 16 with a fluid permeable layer, where the presence of fluid on the outside of the test patch would not be undesirable.

The binder layer 31 may comprise any of a variety of binders depending upon the nature of the volatile analyte to be determined. For example, the binder may chemically bind with the analyte or adsorb the analyte to be determined. Thus, when the analyte being collected is ethanol, the binder layer advantageously contains activated charcoal. In addition, the binder layer may comprise a specific binding partner of the analyte to be determined, such as a polyclonal or monoclonal antibody or an antigen matched to a specific antibody desired to be measured in the perspiration.

The patch 11 is additionally provided with tape 26 or another means for securing the patch to the skin of a subject, as has been detailed in connection with the embodiment illustrated in FIG. 1. Patch 11 is illustrated, however, as having a unitary outer layer 22 extending beyond the perimeter of the underlying layers to form an annular flange 23, which is provided with an adhesive on its lower surface. As discussed in connection with the embodiment of FIG. 1, outer protective layer 22 permits the escape of water vapor yet protects the filter material from chemical contamination from the outside. As also discussed above, gas permeable layer 16 can also in some cases function as the outer layer 22.

C. Dermal Patches Having a Microbead Layer

Figure 3:
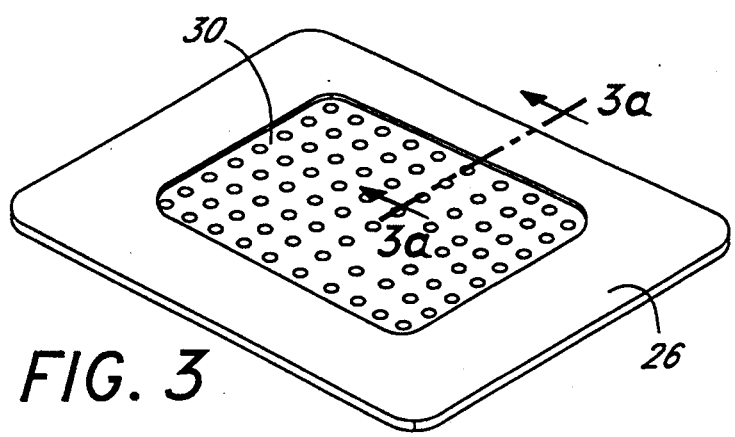
FIG. 3 is a perspective view of a third embodiment of the dermal patch of the present invention.
Figure 3A:
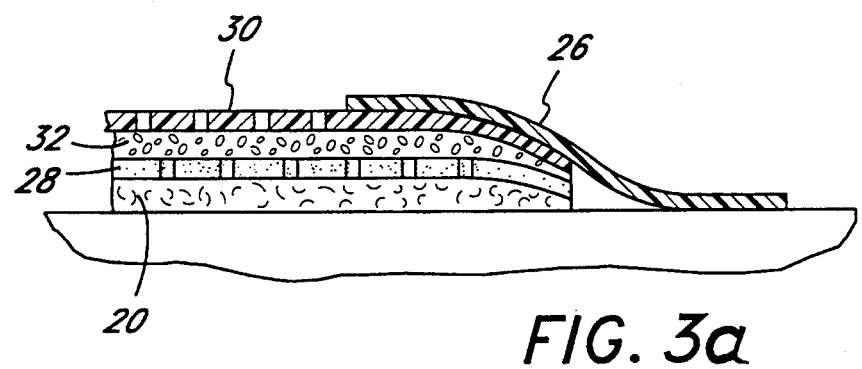
FIG. 3a is a cross-sectional view along the line 3a—3a of the patch of FIG. 3.

Referring to FIGS. 3 and 3a, there is disclosed a further embodiment of the test patch of the present invention wherein an inner porous layer 28 and an outer porous layer 30 define a space for containing a microbead layer 32. The microbeads of such a microbead layer 32 can desirably have attached thereto a capture reagent, such as antibodies or other means for binding analytes of interest. The inner layer 28 and outer layer 30 preferably comprise the same material, which may be any suitable material for providing an unrestricted flow of fluid through the patch while trapping the microbeads in between. One suitable material for porous layers 28, 30 is the fluid permeable and microporous film known by the name Ultipor (nylon 6) and manufactured by Pall Corporation in Glen Cove, N.Y. Additional manufacturers of suitable nylon filtration membranes include Micron Separations, Inc. of Westborough, Mass., and Cuno of Meridan, Conn. Porous layers 28, 30 may also be comprised of materials other than nylon, such as polycarbonate, modified polyvinylchloride and polysulfone.

The gauze, the inner and outer porous layers and the adhesive tape in all embodiments can be cut to size with conventional dies. The gauze 20 and the inner porous layer 28 can be fixed to the adhesive ring 26 with conventional adhesives, such as those used on the adhesive surface itself. Alternatively, they could be heated or ultrasonically bonded together. The proper amount of microbeads can then be placed on top of the inner porous layer, after which the outer porous surface is attached by similar means. Typically, in a one-inch diameter patch, from about 0.05 grams to about 1 gram of microbeads will be used, and preferably from about 0.1 to about 0.4 grams will be used. The inner and outer porous surfaces may have to be staked or spot-welded together in some pattern, as will be appreciated by one of skill in the art, to prevent the microbeads from collecting in one area.

The free adhesive surface is optimally covered by pullaway paper (not illustrated) with adequate space to be gripped with one's fingers. The patch is packaged in a paper or plastic pouch similar to that used in conventional bandaid packaging. The assembled unit could be terminally sterilized or pasteurized prior to sale. Alternatively, the package could comprise a vapor barrier such as a metallic foil or mylar and even include oxygen or moisture absorbent means such as a small packet of any of a variety of known desiccants, such as silica gel, calcium chloride, calcium carbonate, phosphorous pentoxide or others as will be appreciated by one of skill in the art.

The total thickness of microbead layer 32 can be varied considerably. However, if a color change is to be used to detect an analyte and the such color change is to be brought about by immersing the patch in appropriate reagent baths, layer 32 is preferably no more than about 3 mm thick since color changes occurring at immobilized sites on thicker layers would not likely be observable. More preferably, the microbead layer is between about 1 mm and about 2 mm thick. If such color change analysis is not performed, the microbead layer 32 can alternatively be torn open, releasing loose microbeads which can be used to conduct chemical analysis for detecting the presence of an analyte bound to the microbeads by conventional means, such as in a cuvette.

Optimally, the diameter of the beads in microbead layer 32 will be at least about one order of magnitude larger than the diameter of the pores in inner porous layer 28 and outer porous layer 30. For example, the beads contained in microbead layer 32 may have diameters within the range of from about 5 to 50 microns, and preferably within the range of from about 5 to about 10 microns. If 10-micron diameter beads are utilized in the microbead layer 32, for example, inner porous layer 28 and outer porous layer 30 will optimally comprise a median pore size of approximately 1 micron.

The microbead layer 32 may comprise any of a variety of known materials including polystyrene, latex, and glass. Beads sized from approximately 0.05 micron to 100 micron which are suitable for the present application are available from Polysciences of Warrington, Pa.

Microbead layer 32 serves as the support for an immobilized specific binding partner for the analyte to be determined. Thus, a molecule with a high chemical affinity for a specific component in the fluid to be analyzed will be immobilized to the microbeads in microbead layer 32.

D. Dermal Patches Having an Impermeable Outer Layer

Figure 5:
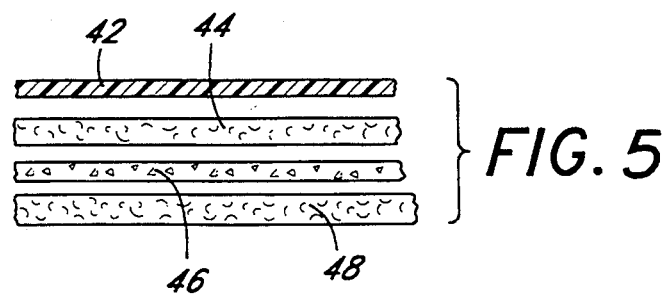
FIG. 5 is an exploded elevational schematic view of a fourth embodiment of the present invention.

Referring to FIG. 5, there is disclosed a further embodiment of the present invention, particularly suited for use under conditions in which profuse sweating is not present, such as in passive insensible perspiration, wherein the test patch is provided with an impermeable outer layer 42. In order to minimize any back diffusion of fluid into the skin, an absorptive layer 44 is provided to form a reservoir for drawing moisture away from the surface of the skin and through support 46 to which is bound a specific binding partner for at least one analyte to be determined. Layer 44 may include chemical means for binding or collecting moisture such as a desiccant, as has been previously discussed, which is suitable for use in proximity to the skin. The patch may be further provided with an underlying porous layer 48 to separate support 46 from the surface of the skin, and the patch is provided with any of the means for attachment to the skin as have been previously discussed.

E. Dermal Patches which Minimize Lateral Diffusion of Sweat in a Patch

Figure 6:
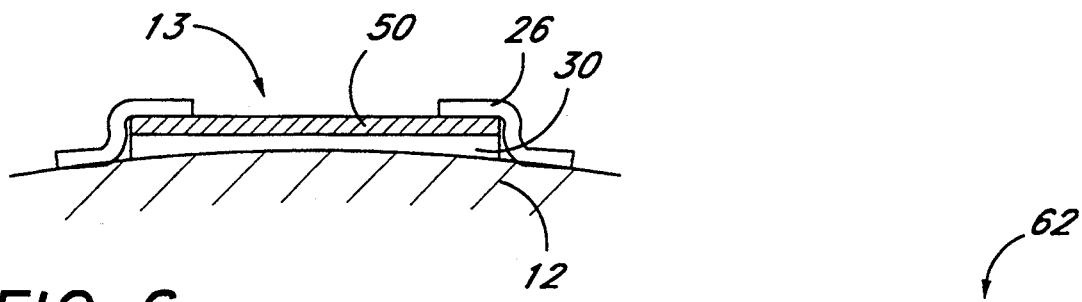
FIG. 6 is a cross-sectional view of a dermal patch according to a further embodiment of the present invention.

Referring to FIG. 6, there is disclosed a modified patch 13 according to the present invention, in which all intervening layers between the skin 12 and the binder layer 30 have been deleted. By disposing the binder layer (i.e., the layer having a specific binding partner for an analyte to be determined) directly adjacent the skin, lateral diffusion of sweat throughout the binder layer 30 is minimized. The proximity of the binder layer 30 to the skin 12 allows the output of each duct of the sweat glands to contact or be in fluid communication with a relatively small area of the binder layer 30. For a variety of reasons which will be apparent to one of skill in the art, it may also be desired to mount a microporous membrane, preferably a fluid permeable membrane 50 atop the binder layer 30.

The evaporative capacity of the binder layer 30 and the fluid permeable membrane 50 is preferably sufficient relative to the output capacity of the individual sweat ducts, to minimize lateral diffusion of sweat away from the immediate area of the duct. This embodiment has special application for monitoring the chemical composition of insensible perspiration and/or non-exercise perspiration, in instances where output from the sweat glands is limited. Due to the magnification effect detailed infra, the present embodiment is also particularly suited for monitoring low concentration analytes.

By limiting the suppressive characteristics of moisture or water on the skin, through the use of materials having a maximal evaporative capacity, the instant embodiment allows increase of the through-put rate of sweat in the patch by maximizing sweat gland output. Nadel and Stolwijk (*J. Applied Physiology*, 35(5): 689–694 (1973)) disclose that sweat gland activity is suppressed by water lying on the skin, finding a difference in whole body sweat rate of 40% between wet and dry skin. Mitchell and Hamilton (*Biological Chemistry*, 178: 345–361 (1948)), found that loss of water and solutes in insensible perspiration presumably stops whenever the surface of the skin is covered with a film of water. Brebner and Kerslake (*J. Physiology*, 175: 295–302 (1964)) postulate that the reason for this phenomenon is that water in contact with the skin causes the epidermal cells of the skin to swell and thus block the sweat ducts.

The ability of the present invention to produce a positive response based upon the presence of relatively low concentrations of analyte is particularly advantageous in view of the fact that, during active exercise, a ¼" diameter area of skin provides approximately 35 microliters of sweat per hour, whereas a similar diameter area of skin produces sweat at a non-exercise rate of only about 3.2 microliters per hour. The present embodiment is further advantageous as not requiring the user to exercise, but only to wear the patch for an equal or typically longer period during rest or at normal activity levels.

Thus, homogeneous diffusion of sweat throughout the binder layer is preferably minimized when using the instant invention in conjunction with insensible and/or non-exercise perspiration and/or a determination of minute amounts of analyte contained within perspiration. The minimized lateral diffusion of perspiration throughout the binder layer 30, according to the present invention, provides a more concentrated collection of sweat at each sweat duct, thereby providing a greater amount of selected analyte to be determined at that area.

F. Dermal Patches Having Multiple Test Zones

Figure 7:
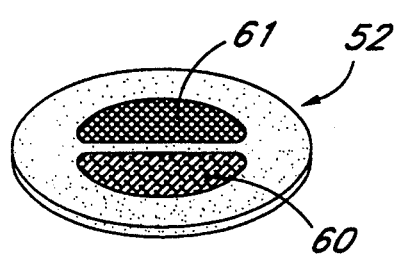
FIG. 7 is a plan view of a dermal patch according to another embodiment of the present invention.

Referring to FIG. 7, there is shown a modified binder layer 52 for a patch according to the present invention, wherein two or more distinct zones are provided on the binder layer 52. The use of a reference zone or of several distinct test zones is contemplated for both the single layer patch discussed in connection with FIG. 6, as well as the embodiments discussed in connection with FIGS. 1-3a and 5. The multi-zone binder layer 52 may also be used for certain embodiments to be discussed hereinafter in connection with FIGS. 6-10 when specific binding chemistry is used.

One or more of the zones, such as determination zone 60 (FIG. 7), is used to test for an analyte of interest within sweat, as detailed previously. One or more of the remaining zones, such as reference zone 61, is used as a reference indicator.

Reference zone 61 performs a variety of functions, depending upon the desired application of the test patch. For example, reference zone 61 can be provided with color change chemistry as discussed previously to provide the wearer with an indication that the patch has been worn for long enough that a sufficient sample volume has traversed the patch to provide a meaningful test for the analyte of choice. For this purpose, reference zone 61 is provided with affinity chemistry for a preselected reference substituent such as IgG, albumin or any other sweat component which is reliably present. Preferably, the selected reference substituent is one which provides a reasonably accurate measurement of the volume of sweat put through the system.

This use of the reference zone 61 may be facilitated by first determining the rough concentration ratio of a reference substituent such as albumin to the analyte to be determined and providing the patch with color change chemistry which provides a visual indication of the presence of the reference substituent only well after the elution of the analyte to be determined has exceeded the lower limits of detection. Reference substituents such as albumin will typically be present in significantly greater quantities than the analyte. Thus, in order to accomplish the objective of indicating passage of a sufficient sample volume, the "sensitivity" of the patch for the reference substituent is preferably lower than for the analyte. This can be achieved by using a proportionately lower amount of a specific binding partner for the reference substituent than for the analyte, other dilutions in the assay, or simply selecting a less abundant reference substituent. Selection of a suitable reference substituent and concentration determinations can be readily made through simple experimentation by one of skill in the art.

G. Use of Dermal Patches Having Multiple Test Zones to Prevent Tampering

Alternatively, and particularly useful in assays for drugs of abuse and their metabolites, a reference zone 61 (FIG. 7) can provide an indication that the skin patch was actually worn by the desired patient, parolee or other subject. One inherent limitation in a test in which a subject desires a negative result is the possibility that the subject will simply remove the patch after administration and replace it just prior to reexamination. This possibility gives rise to the ability of the wearer to ensure false negative results.

However, by provision of a reference zone 61 to detect a known component in sweat, the test results will reveal test patches that have not been worn for the test period. Reference zone 61 thus provides a method of preventing false negative evaluations due to tampering or removal of the test patch.

A reference zone 61 to detect a known component in sweat may also be provided as a positive control zone to ensure the discovery of false negative test results due to degradation of reagents or other components of the patch. In non drug-of-abuse screens, the indication produced within the reference zone 61 will preferably be a visible color change by a chemical or antibody/antigen colorimetric interaction occurring or becoming apparent to the wearer when a predetermined amount of the reference analyte has passed through the interaction area.

Optionally, a reference zone 61 may be provided as a negative control zone to enable the discovery of false positive results. A preferred negative control zone will have an immobilized specific binding partner for an analyte known to be absent in human sweat. The analyte's specific binding partner must be known to not cross react with components present in human sweat. An example of an appropriate analyte is bacteriophage T4 coat protein.

In yet a further embodiment of the present invention (not illustrated) two or more analyte determination zones 60 are provided in a single test patch. The use of multiple test zones is particularly useful in applications such as a drug of abuse screen where testing for any one or more of a wide variety of analytes may be desired. For example, a single test patch may be used to screen for any of a plurality of drugs of abuse, such as THC, Phencyclidine morphine and Methadone. A positive result for any of the drugs on the screen may provide sufficient proof of an offense such as a violation of parole, or can be used to signal the need for more quantitative follow up investigations. Used as an initial screening tool, the present invention offers the advantages of being non-invasive, and much less expensive than conventional quantitative analyses. For these reasons, a screening test patch as disclosed herein is particularly suited for initial screening of large populations such as parolees, inmates, military personnel or others where monitoring is desired.

The analyte determination zone 60 and analyte reference zone 61 may be physically separated on the patch, such as in concentric circles or discrete zones, as illustrated in FIG. 7, or in the case of only two or three analytes, interspersed throughout. In the latter case, positive results of different determinations would be indicated by the appearance of different colors.

II. Placement of Dermal Patches

Although a patch of the present invention can be used to collect analytes contained in any of a variety of body fluids, perspiration is the desired fluid to be collected due to its dependable supply and its similarity to blood, albeit with lower analyte concentrations. Although components found in saliva could also be collected with a patch of the present invention, saliva is often contaminated with molecules not expressed by the body, such as foodstuffs. Therefore, in a preferred embodiment, the patches of the present invention are placed on the skin surface of a subject.

A. Characteristics of Sweat Glands and Perspiration sweat glands are classified to be either of two types. Eccrine type sweat glands function primarily to regulate body temperature through their relationship to evaporative heat loss. It is the eccrine type sweat gland that provides the sweat associated with exercise and is therefore the source of perspiration of interest for many applications of the patch of the present invention. Apocrine type sweat glands are larger secreting elements which are localized only in relatively isolated areas of the body such as the axilla, pubic and mammary areas.

Sato and Fusako (*American J. Physiology*, 245(2): 203–208 (1983)) estimate that the diameter of the duct of the sweat gland is approximately 40 microns. According to Scheupoein and Blank (*Physiological Review*, 51(4): 702–747 (1971)), the average density of sweat glands on the skin surface is approximately 250 per square centimeter. Thus, the total surface area of sweat gland ducts of the skin represent 1/318 of the total surface area of the patch of the instant invention. The visible result on a test patch of the present invention when, for example, using known ELISA technology to determine a low concentration analyte, is the appearance of a number of tiny color changes on the binder or absorptive layer associated with the output of specific ducts. If significant lateral diffusion of sweat is permitted prior to contact with the immobilized binding partner, the color change is frequently too diffuse to detect with the naked eye.

Although the etiology of perspiration is relatively complex, it is known to be caused by both mental states such as mental exercise and emotional stress; thermal stress, as the sedentary body's response to temperature control; and exercise stress as the physically active body's response to temperature control.

In addition to the foregoing distinctions, perspiration can be either insensible or sensible. Insensible sweat appears to be caused by water diffusion through dermal and epidermal layers. Its purpose appears to be not related to thermal regulation at all, but to aid in such things as the improvement of mechanical interaction between the skin and surfaces to facilitate grip. Further complexities arise with regard to the spatial distribution of sweat glands and the flow rates of the various types of perspiration. Specialized areas of the palms and soles of the feet sweat continuously, although at a very low rate. The rate of insensible perspiration is dependent upon the position of the particular area in question relative to the heart. For example, elevating a limb over the heart decreases the insensible perspiration rate in that limb.

At temperatures of about 31° C. in a resting human adult, insensible perspiration proceeds at a rate of between about 6–10 grams per square meter per hour from the skin of the arm, leg and trunk, up to about 100 grams per square meter per hour for palmer, planter and facial skin. The latter three areas jointly account for approximately 42% of the total water loss from the body due to insensible perspiration. Such insensible perspiration first begins on the dorsal surfaces of the foot and spreads to higher places on the body as the temperature increases. One reported study determined that the average water loss due to insensible perspiration for a body surface area of 1.75 square meters ranged from 381 ml, 526 ml and 695 ml per day at ambient temperatures of 22° C., 27° C. and 30° C., respectively.

In contrast to insensible perspiration which does not appear to be associated with a particular surface element of the skin, sensible perspiration has been associated with the eccrine gland. The number of actively secreting eccrine glands varies among individuals and depends upon the part of the body observed and the type of sweat response created. Maximum gland density varies from between about 200 per square centimeter on the forearm to over 400 per square centimeter on the thenar eminence.

The appearance of sensible sweat begins at either when the skin temperature exceeds about 94° F. or the rectal temperature exceeds about 0.2° F. over normal core temperature. Maximum rates of sweat volume loss can be as high as 2 liters per hour in average subjects and can be as high as 4 liters per hour for brief periods. Sensible perspiration begins in the distal parts of the lower extremities and progresses upward as the environmental temperature is elevated. Thus, the dorsum of the foot begins to sweat long before the chest. The pattern of sensible sweat response also shifts from one region of the body to another as the thermal stress increases. Under mild thermal stress, sweating is present mainly in the lower extremities. As the thermal stress further increases, sweating spreads to the trunk. Due to its large surface area, the trunk becomes the dominant water loss surface. Eventually, extremely high rates are found in the trunk while rates in the lower extremities may actually decline. The forehead can produce extremely high sweat rates but is among the last areas to sweat in response to thermal stress.

B. Placement of Dermal Patches

Although a patch of the present invention can be worn at any practical location on the body, preferable locations for the patch include the skin on the sole of the foot and areas on the chest, back, and biceps. The patch is able to be worn in confidence in these areas, and these areas are not covered with excessive hair, so that the patch may be secured with conventional adhesive tapes.

The patch can advantageously be located on different regions of the body depending upon a variety of factors. It is well known that the quantity of perspiration generated is a function of both the location on the body, as well as the physical activity during and immediately preceding collection. This is due to both different densities of sweat glands on different regions of the body, as well as to certain regulatory functions of those glands.

Other desirable placement locations for the patches of the present invention will depend on the conditions under which it is desired to detect analytes. Using the parameters described above and other known factors, one of skill in the art will understand how to choose a desirable location on the body of a subject on which to place a patch.

III. Chemical Species Detectible with a Dermal Patch

A large variety of chemical species which are detectable in blood are also present in sweat, although typically in a much lesser concentration. Early investigation into the composition of perspiration centered on electrolytes, including sodium, chloride, calcium and potassium. Extreme individual variation was found among individuals, and the electrolyte composition also differed depending upon whether the sweat was stimulated by thermal, mental or other etiology.

Further research has identified numerous additional components in sweat, including both electrolytes and more complex biological molecules. Some illustrative chemical species which have been identified in sweat are identified in Table I below.

TABLE I

| Chemical Components of Sweat | |
|---|---|
| diphtheria antitoxin | sulfates |
| ascorbic acid | iodine |
| thiamine | iron |
| riboflavin | fluorine |
| nicotinic acid | bromine |
| amino acids | bismuth |
| ethanol | lactic acid |
| antipyrine | pyruvate glucose |
| creatinine | nitrogen |
| C-14 methylurea | ammonia |
| C-14 acetamide | uric acid |
| C-14 urea | nicotine |
| thiourea | morphine |
| paraaminohippuric acid | sulfanilamide |
| mannitol sucrose | atabrin |
| lactate | methadone |
| sodium chloride | phencyclidine |
| potassium | aminopyrine |
| calcium | sulfaguanidine |
| magnesium | sulfadiacine |
| phosphorous | amphetamines |
| manganese | benzoylecgonine |
| theophylline | phenobarbital |
| parathion | androgen steroids |
| tetrahydrocannabinol | phencyclidine |
| insulin | phenytoin |
| cimetidine | carbamazepine |
| dimethylacetamide | |

Any of the entries in Table I for which affinity chemistry can be developed can be an appropriate subject of a test patch according to the present invention. Since most of the components listed in Table I are nonvolatile, they will be trapped in the concentration zone 14 of the patch 10 illustrated in FIG. 1a, or on the binder layer 30 of FIG. 6. However, some components, most notably ethanol, would volatilize under the influence of body heat, thereby enabling escape in the vapor phase through the test patch. Where the analyte to be determined is ethanol or another volatile component, a patch of the present invention may be modified as described in connection with the embodiment illustrated in FIG. 2 to contain specific binding partners for the analyte.

In one preferred embodiment, the analyte to be determined in perspiration is the enzyme creatine kinase MB (CK-MB) which is expressed from the cardiac muscle during myocardial infarction and other cardiac distress. A monoclonal antibody raised against CK-MB can be immobilized to the microbeads in accordance with any of a variety of conventional methods, such as the cyanogen bromide technique described in Pharmacia product literature (Pharmacia, Inc., Piscataway, N.J.).

The antibody which is to be used for the purpose of complexing with CK-MB may be immobilized on any of a variety of supports known in the art. For example, anti-CK-MB antibody may be bound to polysaccharide polymers using the process described in U.S. Pat. No. 3,645,852. Alternatively, the antibody may be bound to supports comprising filter paper, or plastic beads made from polyethylene, polystyrene, polypropylene or other suitable material as desired. Preferably, the support will take the form of a multiplicity of microbeads which can conveniently be formed into microbead layer 32, illustrated in FIG. 3a.

Figure 1A:
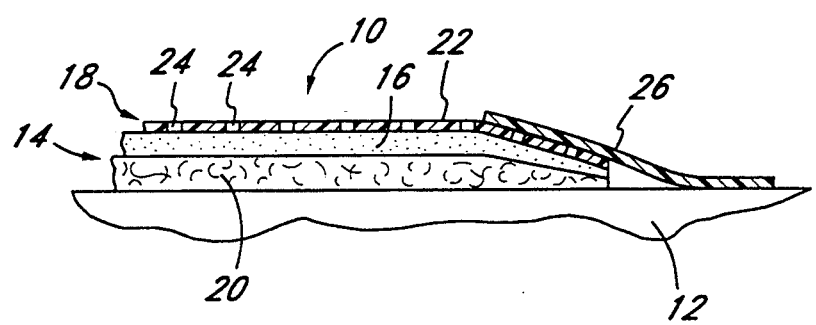
FIG. 1a is a cross-sectional view along the line 1a—1a of the dermal patch of FIG. 1.

As an alternative to a microbead support layer, the specific binding partner could be immobilized directly to the inner porous layer 20 or 28 on FIG. 3a, to the underside of filter 16 of FIG. 1a, or to appropriate absorbent materials used in any of the embodiments of the dermal patch. In this manner, the need for microbead layer 32 could be eliminated entirely. Fluid permeable membranes which are specifically designed for binding antibody proteins are commercially available, such as Zetapor from Cuno, and Protrans, available from ICN in Costa Mesa, Calif.

The monoclonal antibodies useful in the present invention can be produced and isolated by processes which are well known in the art, such as those discussed by Milstein and Kohler, reported in Nature, 256: 495–497 (1975). In particular, Jackson describes a method of producing anti-CK-MM (an indicator of the status of skeletal muscles) and anti-CK-MB antibodies in Clin. Chem., 30/7: 1157–1162 (1984)).

Alternatively, the components of a commercially available diagnostic kit can be utilized which incorporate the CK-MM enzyme chemically bound to a bead support. A suitable kit marketed as the Isomune-Ck Diagnostic Kit by Roche of Nutley, N.J., is one commercially available candidate. This kit includes a goat antisera to human CK-MM and donkey anti-goat antibody covalently bound to styrene beads. A mixture would produce an immobilized conjugate having a specific affinity for human CK-MM. A more direct and less expensive procedure, however, would be to immobilize the anti-CK-MM monoclonal antibody directly to the microbead support in accordance with methods now well known in the art.

IV. Detecting Analytes

A. Using Color Change Chemistry to Detect Analytes

Figure 4:
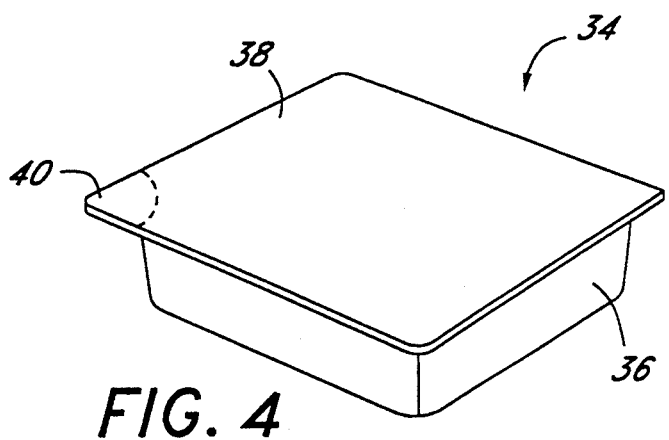
FIG. 4 is a perspective view of one embodiment of a reagent packet for use in effecting a color change responsive to the presence of analyte in the patch of the present invention.

Any of a number of methods known to the art can be used to detect an analyte collected on a patch of the present invention. One such method involves the use of color change chemistry to visualize the presence of an analyte on a patch. In this embodiment, after the test patch has been worn for a suitable period of time, it can be removed by the wearer (in non-drug screen tests) and developed to produce a visible indicium of the test result. Such a test patch can be marketed together with a developer packet such as packet 34 shown in FIG. 4 which contains known developer reagents for the immuneassay. The reagent packet 34 comprises a container 36 having a removably secured top 38. A flap 40 on the top 38 of the reagent packet facilitates gripping the top 38 and peeling away from container 36 to reveal the reagent contained therein. As an example, a protein electrophoresis stain such as Coomassie brilliant blue or amido black 10b, can be bound to purified analyte contained in the reagent packet 34. When a test patch is immersed in the packet 34, any antibodies on the test patch that are unbound by analyte in the perspiration will become occupied by stained purified analyte in the packet 34. There will thus be an inverse relationship between the amount of stain absorbed by the patch and the amount of enzyme passed through the patch. In this embodiment, the user would place the patch in the fluid of the packet 34, wait for some period of time such as 30 seconds or more, rinse the patch under tap water and relate the resultant color of the patch to the presence of the enzyme. A color comparison chart and control zone on the patch having no bound antibody may be provided to aid in this interpretation.

Alternatively, the user could support the test patch on an open vessel, such as a small jar or vial, or empty container similar in design to reagent packet 34 securing the adhesive border of the patch to the rim of the vessel, and then pour contents of packet 34 on top of the test patch. Gravity would assist the transport of the contents of packet 34 through the test patch to maximize the efficiency of the stain/binding reaction, and to facilitate visualization of the color change.

The system could readily be designed so that the user performs the interpretation of the concentration of the analyte not in the patch at all but by observing the packet contents once the contents have traversed the patch. This method would be similar to conventional ELISA assay methods where the packet contents contain enzyme conjugates which will react to specific enzyme substrates. The enzyme substrates would be added to the packet contents after those contents transversed the test patch.

If the perspiration contained molecules of interest, they would bind to the specific immobilized binding partner on the patch. If this occurred, enzyme conjugates in the packet would pass freely across the test patch and enzymatically modify the enzyme substrate producing a controlled color change in the solution in the packet. If the perspiration contained the desired molecules of interest, enzyme conjugates would then be bound in transit across the patch and would be unavailable to cause color change in the substrate solution. Other immunoassay schemes can be readily adapted for use in the present invention by one of skill in the art.

A variety of well known immunoassay schemes for visualizing the presence of an analyte of interest are well known in the art, and need not be detailed here. However, the optimal immunoassay scheme is generally one which is simple and requires the fewest steps. For many types of assays, it will be desirable for the wearer to obtain rapid results such as a color change to demonstrate a positive or negative result with as few steps as possible. On the other hand, drug of abuse screens are more likely to be evaluated by clinical staff instead of by the test subject, and there is less concern for a "user friendly" product.

For example, in a patch of the present invention designed for determining both the presence of CK-MM and CK-MB enzyme, the immobilized specific binding partner for each of those enzymes will be segregated to separate regions of the test patch. In this manner, if an enzyme-linked immunoassay system is utilized, a common enzyme and a common substrate could be used. Alternatively, a different color can be used to express the presence of different analytes.

B. Detecting a Metabolite of an Analyte Collected on a Patch

One problem which has been encountered in detecting analytes contained in patches, especially when such analytes are drugs of abuse, is that many conventional systems for performing drug testing do not test for the analytes which are collected on a patch but rather for the metabolites of such analytes. This is because the analytes themselves are not expressed in some body fluids. For example, cocaine is present in perspiration but not in urine. Therefore, urine is not tested for the presence of the cocaine molecule itself but rather for the presence of the major urine metabolite of cocaine in man, benzoylecgonine ("BE"), in order to detect cocaine use by a subject.

Currently, the primary method for the diagnosis of drug abuse is by urine analysis. Many conventional diagnostic systems, therefore, are designed to screen for drug analytes (or their metabolites) in urine. For example, numerous companies have developed very sophisticated automated systems to quantify cocaine metabolites in urine. Such systems are highly sensitive to the presence of the major cocaine metabolite in human urine, benzoylecgonine or BE. However, since the cocaine molecule itself is not present in urine, many of these systems, such as the SYVA EMIT system (Palo Alto, Calif.) and Roche RIA system (Nutley, N.J.), are virtually blind to the cocaine molecule itself.

In order to take advantage of conventional diagnostic systems that perform drug abuse testing by urinalysis, it is important that the drug contents of a patch of the present invention be measurable by such diagnostic systems. Unfortunately, most of the kits on the market which test for the presence of analytes such as cocaine are designed to detect metabolites of such molecules rather than the analytes themselves. In order to utilize such diagnostic systems to test for a desired analyte, therefore, the contents of a patch must be chemically modified.

In accordance with another aspect of the present invention, therefore, an analyte contained in a patch which is not detectable by conventional diagnostic systems, particularly systems for performing urinalysis, is chemically modified so that it can be detected by such systems. In this aspect, an analyte passed through the skin of a subject in perspiration is collected on an absorbent material in the patch. The analyte can then be chemically modified and detected while still in the absorbent layer or while bound to a microbead in a microbead layer. Alternatively, the analyte can be freed from the absorbent material, such as through chemical elution or by dissolving the absorbent material, in order to allow the analyte to be detected by a conventional diagnostic system. The analyte is then chemically modified so that it can be detected in such a diagnostic system.

As long as the analyte and the metabolite of that analyte which is detected by a diagnostic system are known and a means of converting the analyte into its metabolite is known, it is within the knowledge of one of skill in the art to chemically modify such an analyte so that it can be detected. Thus, any such analyte contained in a patch of the present invention can be tested using conventional diagnostic systems. However, an example of how to chemically modify a particular analyte commonly tested for, cocaine, will be detailed below.

Cocaine is metabolized in the body by either pH changes or cholinesterase enzymes. Cocaine is unstable at pH values higher than 7, and thus can be converted to BE either through exposure to high pH or to cholinesterase enzymes. Therefore, in order to chemically modify the cocaine on a patch and convert it to BE in order to make it detectable by conventional urinalysis, cocaine molecules can be extracted from the patch and then exposed to a solution at pH 11 at room temperature for 10 minutes or more. Following this modification step, the patch extract is returned to a neutral pH and then analyzed with conventional diagnostic systems. As is obvious to one of skill in the art, other methods of hydrolyzing the ester linkages of the cocaine molecule in order to produce BE, such as through the use of enzymes, can also be performed in order to prepare an extract of a patch of the present invention so that it can be detected by conventional diagnostic systems.

C. Eluting Analytes from Dermal Patches

Another difficulty encountered in detecting analytes that are contained in perspiration and collected on a patch is that, unless color change chemistry is used to detect such analytes, these analytes usually have to be removed from the patch in order to detect them. Removing the analytes normally involves chemically eluting them from the patch, which is both labor intensive and time consuming.

Therefore, in yet another aspect of the present invention, a patch is provided in which the absorbent material of the patch on which analytes are collected is dissolvable. When such absorbent material is dissolved, the analytes contained therein are made available for detection through further diagnostic procedures. As in other embodiments of a patch of the present invention, a patch incorporating a dissolvable absorbent material is placed in fluid communication with the skin of a subject in order to collect analytes contained in perspiration. Such a patch also preferably contains a gas permeable layer between the absorbent material and the outside of the patch in order to allow the fluids expressed through the skin in perspiration to escape to the outside of the patch in their vapor phase.

The analytes of interest that are collected on the absorbent material are preferably able to withstand the chemical treatment which results in the dissolution of the absorbent material. Thus, the dissolution of the absorbent material will not affect the analysis of the analytes contained in the absorbent material. One of skill in the art will be able to recognize whether a particular analyte will be chemically changed by a particular chemical treatment used to dissolve the absorbent material. If one of skill in the art would be unsure as to whether a particular analyte would withstand such chemical treatment, it is a matter of routine experimentation to treat a sample of the analyte under the conditions of the chemical treatment and then determine whether the analyte has been chemically altered.

In another embodiment, the chemical treatment of the absorbent material converts an analyte of interest contained in the absorbent material into a detectable metabolite or into some other detectable species. For example, the treatment of cocaine with a strong base converts it into BE, a common cocaine metabolite found in urine. The same strong base can also be used to dissolve an absorption disk made from a material sensitive to strong bases. In this embodiment, the dissolving of the absorbent material does not interfere with the analysis of the analyte contained in the absorbent material, but instead actually allows the analyte to be analyzed.

An absorbent material for use in this aspect of the present invention can be made from any of a variety of materials which can be chemically dissolved. For example, a number of materials are variously susceptible to chemical attack and dissolution by acids and/or bases. Among these materials are Nylon 6/6 (sold as Vydyne 909 by Monsanto Co., St. Louis, Mo.), Phenolic (sold as Polychem 102 by Budd Co.), Polyester (PBT) (sold as Celanex 3300-2 by Celanese Plastics), and polyurethane (TP) (sold as Pellethane 2363-55D by The Upjohn Co.). To dissolve any of these materials, an appropriately strong acid or base is added the material, as is known to those of skill in the art.

Absorbent materials can also comprise a woven protein web, such as a web made from protein fibers approximately 0.03 inches thick. Such fibers are disclosed by Baumgartner, *J. Forensic Sciences*, 34: 1433–1453 (1989)).

Another dissolvable material which can be used as the absorbent material in the patch of the present invention is polystyrene. In this embodiment, solvents of polystyrene can be used to dissolve such absorbent material. Such solvents include chlorinated and aromatic hydrocarbons, esters, ketones, essential oils of high terpene content and turpentine. Specific examples of such solvents include cyclohexanone, dichloroethylene, and methylenedichloride.

Materials and solvents other than those listed above, of course, can also be used in this aspect of the present invention. The foregoing materials and solvents are therefore exemplary of this aspect of the present invention and not intended to be limiting.

V. Quantitative Determination of an Analyte in Perspiration

A. Dermal Patches for the Quantitative Determination of an Analyte

In another aspect of the present invention, the amount of an analyte that is present in a given volume of a subject's perspiration can be discovered. An embodiment of this aspect of the present invention is illustrated in FIG. 11. In this embodiment, a fluid permeable support layer 120 is in fluid communication with the skin 12 of a subject mammal, such as a human, and is located between the skin 12 of the subject and an absorptive layer 130 made of an absorptive material.

In the embodiment illustrated in FIG. 11, the support layer 120 also comprises a rate-limiting structure which limits the passage of perspiration from the skin 12 to the absorptive layer 130 to a rate lower than the rate of insensible perspiration of the subject. The insensible rate of perspiration is the rate of continuous perspiration of a subject which occurs without regard to the regulation of the temperature of the subject and which is not normally noticed by that subject. For humans, the rate of insensible perspiration of sweat glands in the arm, leg or trunk is approximately 6–10 ml/m*m*hr (Randall, W. C., *Am. J. Phys. Med.*, 32: 292 (1953)). Since the rate of perspiration of the subject will almost always be equal to or greater than the rate of passage of such perspiration through the rate-limited support layer 120, the rate of perspiration passing into the absorptive layer 130 can be kept approximately constant.

The rate-limited support layer 120 can be made from any material which can control the rate of diffusion of the components of perspiration. For example, diffusion can be controlled by a membrane. The rate of diffusion of any particular membrane is related to physical characteristics of the membrane such as its molecular composition, thickness, and, in the case of a porous type of membrane, its pore size. One example of a porous type of membrane which can be used as a rate-limited structure in this embodiment of the present invention is a polyester-supported polycarbonate microporous membrane, such as that manufactured by Nuclepore (Menlo Park, Calif.). The pore density, pore size and thickness of the membrane can be adjusted to provide the necessary limited fluid transport rate for this application. Another example of a porous membrane is nylon 6,6, such as that manufactured by Pall Corp. (Glencove, N.Y.).

An alternative to using a porous type rate-limited membrane is to use a rate-limiting structure comprising a dialysis or osmotic non-porous membrane. Such membranes have the advantage of having molecular weight specificity, which may increase analyte sensitivity. For example, if one were interested in collecting a therapeutic drug or its metabolites in the absorptive layer 130 and these analytes had a molecular weight of 1000 Dalton, one could choose a dialysis membrane which would pass only molecules which are smaller than 2000 Dalton in size. Larger molecules would be excluded from passing into the absorptive layer 130. By limiting the molecules which pass into the absorptive layer 130, interference by other components in perspiration in the laboratory analysis of the analyte in the absorptive layer 130 is minimized. Although the support layer 130 of this embodiment of the invention has been described as comprising a rate-limited structure, one of skill in the art will recognize that the support layer 130 and the rate-limited structure can be two separate membranes or structures in fluid communication with each other.

The absorptive layer 130 is located distally of the support layer 120 so that said support layer 120 is between the subject's skin 12 and the absorptive layer when the patch is being worn. The absorptive layer can be made from any number of absorbent materials. If passive absorption of an analyte is adequate to capture that analyte on the patch, then a layer of medical grade paper such as Filtration Sciences medical grade paper (FS#39) will suffice. If active absorption is required then substances such as monoclonal antibodies specifically tailored for high affinity to the analyte can be chemically coupled to the absorptive layer 130 in order to concentrate the analyte on the absorptive material, as previously described.

In this embodiment of the invention, a gas permeable layer 140, which in a preferred embodiment is also an outer protective layer, is located distally from the skin 12 of the subject on the side of the absorptive layer 130 opposite that which borders the support layer 120. The gas permeable, outer protective layer 140 can be made, for example, from 1625 Tegaderm wound dressing made by the 3M Company (St. Paul, Minn.). In a preferred embodiment, the gas permeable layer 140 extends beyond the areas of skin 12 covered by the support layer 120 and the absorptive layer 130 when the dermal patch 110 is applied to the skin 12 of a subject. In this way, the support layer 120 and absorptive layer 130 are protected from external abrasion and wear.

A means for attaching the patch to the skin of a subject is also preferably applied to a portion of the outer protective layer 140 which extends beyond the support layer 120 and the absorptive layer 130. Most commonly, the means for attaching is an adhesive composition. For example, in a patch 110 in which the outer protective layer 140 (excluding that portion to which an adhesive is applied) is approximately 14 cm², an adhesive can be applied to an area of approximately 1 cm around the outer perimeter of the outer protective layer 140 on the side of the outer protective layer 140 in contact with the subject's skin in order to attach the patch 110 to the skin 12 of a subject.

In a more preferred embodiment, a pooling area 150 is formed between the outer protective layer 140 and the subject's skin 12 when the patch is worn on the subject's skin 12. Such a pooling area 150 can be formed, for example, by an area 152 of the outer protective layer 140 which extends beyond the support layer 120 and the absorptive layer 130 and to which no adhesive is applied. Such a pooling area 150 collects the excess perspiration that is not diffused across the support layer 120 and allows it to dissipate into the environment across the outer protective layer 140. By providing such a pooling area, the back-diffusion of the components of perspiration across the skin 12 is minimized, since excess perspiration which is unable to pass into the absorptive layer 130 is shunted into the pooling area 150. Since the rate of flow of perspiration into the absorptive layer 130 is controlled by the rate-limiting structure of the support layer 120, the absorbent material of the absorptive layer 130 is in fluid communication with the pooling area 150 only through the support layer 120.

This pooling area is unattached to the subject's skin, and provides a sufficient amount of space to accommodate extra perspiration which does not pass across the rate-limited structure of the support layer 120. For example, during times of heavy exercise, the rate of perspiration of the subject might rise well beyond the rate at which perspiration can be passed into the absorptive layer 130. During such times of heavy perspiration, the pooling area 150 acts as a "shunt" to divert perspiration away from the support layer 120. The volatile components of such perspiration then evaporate through the gas permeable layer 140. In this way, the back-diffusion of perspiration and the buildup of bacteria under the rate-limited structure of the support layer 120 can be avoided or at least mitigated.

B. Using Dermal Patches to Determine the Amount of an Analyte in Perspiration

In order to determine the length of time a patch has been worn, the amount of a reference analyte contained in a certain volume of perspiration of a subject must first be determined. This analyte must be present in an approximately constant amount in a given volume of perspiration for the period of time that the patch is worn by a subject. Once such an analyte and its concentration in perspiration is known, the amount of time a patch is worn can be determined because the rate at which perspiration passes into the absorptive layer is held approximately constant by the rate-limited structure. Since the rate of passage of perspiration is known and the amount of the reference analyte in a given volume is known, once the total amount of the analyte in absorptive layer is known the amount of time the patch has been worn by a subject can be determined.

The volume of perspiration concentrated on a patch can also be determined through the use of this embodiment of the present invention. The rate-limited structure of the support layer 120 in this embodiment is preferably designed to allow the passage of perspiration to the absorptive layer 130 at a rate lower than the minimal rate of passage of perspiration through the skin, thereby assuring a relatively constant rate of flow of perspiration into the absorptive layer 130. The total volume of perspiration concentrated on the absorption disk is thus directly related to and can be determined by the duration of wear.

In order to quantitatively determine the amount of an analyte contained in a given volume of a subject's perspiration, a patch having a rate-limited structure as described above is first placed on the skin of a subject, preferably a mammal. Perspiration is then passed across this rate-limited structure at a known rate. For example, if the rate at which perspiration is allowed to pass across the rate-limited structure is equal to or less than the insensible rate of perspiration of the subject, perspiration will pass into the absorbent material at approximately a constant rate. After a sufficient test period of time has elapsed to allow a detectable amount of the analyte to be tested for to pass into the absorbent material, the patch is removed from the skin of the subject. When the patch is removed, the amount of time between the placement of the patch on the skin of the subject and the removal of the patch is recorded.

In order to then determine the total volume of perspiration which has passed into the absorptive layer 130 and concentrated analytes there, the rate of flow of perspiration into the absorptive layer 130 (as determined by the rate at which perspiration passes across the rate-limited structure of the support layer 120) is first multiplied by the amount of time the patch has been worn. This figure indicates the volume of perspiration which has passed through the support layer 120 and into the absorptive layer 130. The total quantity of analyte in the absorptive layer is then determined. By dividing the total amount of analyte present by the total volume of perspiration which has passed into the absorptive layer 130, the average amount of the analyte in a given volume of the subject's perspiration can be determined.

The above described aspect of the present invention is thereby suited to be used in many areas of diagnostics where quantitative information about a particular analyte is necessary. For example, this invention can be used to monitor therapeutic drug administration, determine the nutritional adequacy of a subject's diet, or explore hormonal imbalances in a particular subject.

VI. Prevention of Tampering with Dermal Patches

In some uses of the present dermal patches, it is advantageous to provide a means for indicating whether a wearer has removed a patch during the examination period, particularly in situations where a wearer has an incentive to make sure that the patch produces a specific result. For example, if it is desired to determine whether a wearer has ingested a drug of abuse, safeguards are desirably provided to prevent tampering with the dermal patch.

A. Dermal Patches with Radial Slits

Figure 8:
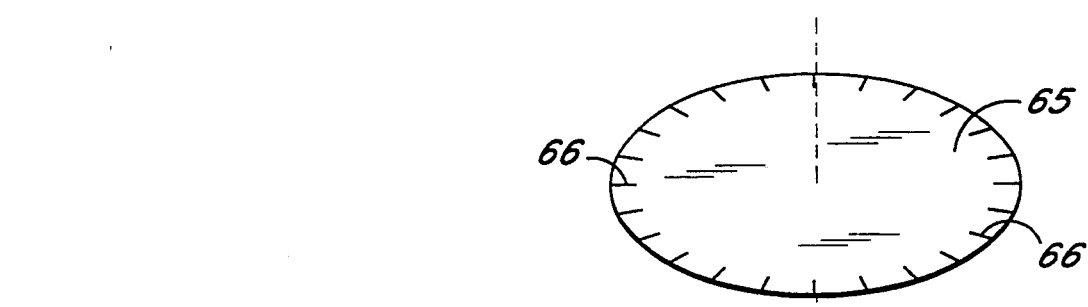
FIG. 8 is an exploded elevational view of a dermal patch according to yet another embodiment of the present invention.

One embodiment of a patch for preventing tampering is illustrated in FIG. 8. In this embodiment, the patch 62 is secured to the skin 64 with an adhesive member 65. The adhesive member 65 is preferably constructed of a material that is strong enough to hold the patch 62 to the skin 64, but that is relatively easily torn such as during removal of the patch from the skin. A suitable material for use in this preferred embodiment is Tegaderm 1625, manufactured by Minnesota, Mining, and Manufacturing Corp. of St. Paul, Minn. Other companies, including Avery and Johnson & Johnson, manufacture similar suitable materials; the Johnson & Johnson product being sold under the trademark "Bioclusive." It has been found, however, that with sufficient patience, a wearer could remove an adhesive member of this type and replace it without leaving any visible indication that the adhesive member has been removed. Therefore, in the particularly preferred embodiment shown, the adhesive member 65 has stress razors 66 in the form of a plurality of radial slits around its outer perimeter. The stress razors 66 can be arranged in any of a wide variety of configurations and densities and accrue the advantage of tearing upon removal, as will be apparent to one of skill in the art.

In the embodiment illustrated in FIG. 8, the radial slits 66 extend approximately 0.05 inches in length from the outer edge toward the center of the patch 62. The slits 66 may be arranged with any of a variety of regular or irregular spacings therebetween, and, in the preferred embodiment are preferably spaced approximately every 0.10 inches around the perimeter of the patch 62. The adhesive force of the material of the adhesive member 65 is preferably more than the force needed to tear the adhesive member at the stress razors 66, so that if the patch 62 is removed, the material of the adhesive member is torn. Thus, when a patch of this preferred embodiment is worn, a torn adhesive member serves as an indication that the wearer has likely tampered with the patch. Of course, the weakening of the adhesive member 65 may be accomplished by providing perforations rather than slits and the slits or perforations may be oriented in directions other than radially.

During storage prior to use, it is desirable to cover the adhesive member to prevent it from sticking to any surface; otherwise the stress razors 66 could become torn prior to use. Accordingly, in the preferred embodiment shown in FIG. 8, the patch is provided with an inner cover 69 to protect the adhesive member 65. The inner cover 69 is removed to expose the adhesive member 65 prior to application of the patch 62 to a subject's skin. Any of a variety of non-adherent materials known to those of skill in the art may be used for the inner cover 69, such as those commonly used to cover adhesive bandages.

The patch 62 is virtually impossible to remove and replace without showing visible signs of tampering. Thus, any analytes in sweat produced from skin under the concentration zone 14 during the time the patch is worn should be present in the patch.

However, a particularly shrewd subject desiring to produce false negative results could obtain additional test patches. This shrewd subject would obtain false negative results by removing the initially applied test patch and replacing the test patch just prior to the time the patch is to be removed for assay. In order to ensure that the patch removed from the subject is the same patch which was initially applied to the subject, an identifying marker which is difficult to reproduce can be incorporated into the patch. For example, a bar code identification strip 67, similar to the bar codes used at supermarket check out stands can be incorporated into the patch, preferably just below the adhesive member 65. For best results in protecting against replacement of the patch, it is important that the identifying marker not be easily removed and replaced without providing an indication that the patch has been tampered with.

In a preferred embodiment, the patch 62 has a filter 68 between the outer layer 65 and concentration zone 14, as described above in connection with FIGS. 1–3a. In a particularly preferred embodiment, the filter is a fluid permeable filter formed from a James River Paper Drape.

The preferred adhesive members of the embodiment shown in FIG. 8, made from adhesive materials, such as Tegaderm, which are relatively weak in strength, have generally been designed for hospital patients who are not expected to perspire at high rates. Therefore, the moisture vapor transmission rate (MVTR) of these materials is relatively low. For example, the MVTR of Tegaderm is approximately 810 g/m*m*day. However, an active person may perspire at instantaneous rates as high as 26000 g/m*m*day. Consequently, an active person may put out more sweat than these adhesive members can transmit to the atmosphere. If this sweat accumulates for any significant period of time, channels may be formed between the skin 64 and the adhesive member 65, allowing sweat to exit between the adhesive member and the skin, rather than be absorbed by the patch 62.

B. Dermal Patches with Pinhole Perforations

In accordance with a further embodiment of the present invention for preventing tampering, illustrated in FIG. 9, there is provided a patch 70 having an adhesive member 72 which allows excessive sweat to be freely transmitted to the outside through pinhole perforations 73. The pinhole perforations may be distributed throughout a wide band 75 extending from the outer perimeter of the adhesive member to a narrow band 77 surrounding the test region 821 of the patch 70.

Sweat produced beneath test region 81, over which there are no pinhole perforations 73, will be absorbed by the test region and will not be transmitted to the outside. The test region 81 includes the area of the patch 70 directly under the concentration zone 14 of the patch as well as the area immediately outside this zone. The narrow band 77 outside the concentration zone 14 of the patch has no pinhole perforations 73, and substantially restricts sweat forming underneath the test region 81 from communicating with the wide band 75 where sweat is transmitted to the outside.

The width of the narrow band 77, is preferably between 0.025 and 0.250 inches, more preferably between 0.05 and 0.125 inches. Narrow band widths less than the preferred width are not expected to keep contact with the skin, whereas narrow band widths greater than the preferred width may allow sweat channels to form, creating a path for sweat forming within the test region 81 to communicate with the outside.

C. Use of Soluble Markers to Prevent Tampering

A wearer of the patch in screenings for drugs of abuse would be expected to be rather creative in circumventing the protections of the patch. For example, a creative wearer could try to wash out the concentrated sweat components from the patch while the patch remains on the wearer's skin. Such washing could be attempted using a needle and syringe, such as those commonly used by intravenous drug abusers for drug injection. For those patches employing specific binding chemistry, attempted elution of the concentrated components using water would likely prove unsuccessful. Even for those patches not employing specific binding chemistry for the analyte being tested, elution with water alone would be difficult, requiring substantial volumes of water without triggering the detection of tampering through the removal of the patch from the skin. However, certain analytes could successfully be at least partially eluted using other solvents.

Thus, in order to detect tampering with the patch through elution of the patch's contents using water or other solvents, a known amount of a marker which is readily soluble in either aqueous or non-aqueous solvents, can be added to the concentration zone during manufacture of the patch. The marker should be easily quantifiable. The marker should also be soluble in either aqueous or non-aqueous solvents depending on the likely route of elution of the analyte. Additionally, the marker should be suitable for prolonged skin contact and not be readily absorbed by the skin. A variety of dyes used in the production of makeup have these suitable characteristics. Oil red N (catalogue number 29,8492) sold by Aldrich Chemical Corp. of Milwaukee, Wis. is a suitable lipid soluble dye. DG01 red and DH60 yellow, both available from Virginia Dare Extract Co. of Brooklyn, N.Y. are suitable water soluble dyes. These water soluble dyes can be easily quantitated by elution from the patch followed by measuring optical density at 6500 nm for the red or 5800 nm for the yellow dye. The quantity of dye remaining can be compared with the range of the amount of dye found to be remaining in patches worn continuously without tampering for the same length of time.

Non-visible markers could also be used to prevent the wearer of the patch from obtaining feedback regarding the extent of marker remaining in the patch. A colorless protein could be used for this purpose. A protein should be chosen that is easily identified in the lab, and also not be expected in human sweat. For example, Bovine gamma globulins, such as those sold by Sigma Chemical Co. of St. Louis, Mo., could also be used as a marker. The presence of these markers can be easily ascertained using Bovine IgG RID kit, available from ICN of Costa Mesa, Calif.

Thus, when a suitable marker is employed within the patch, when the patch is analyzed for the particular analyte being tested, the patch can also be analyzed for the presence of the marker. For visible markers, such as makeup dyes, the presence of the marker may be analyzed by simply viewing the patch. For non-visible markers, the non-visible marker can be assayed along with the analyte. A significant decrease in the amount of marker present would be an indication of tampering through elution of the patch with a solvent.

D. Use of Adulterants to Prevent Tampering

A further method of tampering with the patch would be to add an adulterant to the patch which interferes with the assay chemistry. Numerous materials have been used to adulterate urine tests for drugs of abuse. The most commonly used, and generally most effective method of producing a false negative result in a urine test is to dilute the urine by ingestion of excessive amounts of fluids. Advantageously, this approach would not likely be successful in producing false negative results in the sweat collection patch of the present invention because interstitial concentration of drug metabolites is less likely to be influenced by ingestion of fluids.

However, the addition of certain adulterants to the patch may interfere with the analysis chemistry. For example, acids and bases are known to interfere with assays for many drug metabolites by altering the metabolites' molecular structure. Additionally, many household products, such as detergents, ammonia, ascorbic acid (Vitamin C), and drain openers have been used to interfere with urine assays. These products produce extremes of pH or changes in other chemical parameters, and would be expected to result in trauma to the skin if used in connection with tests using the patch of the present invention. This trauma could be noted by the technician removing the patch.

However, weak acids and bases, as well as eye drops sold under the trademark "Visine," are also known to interfere with a variety of assays for drug metabolites in urinalysis. However, these materials would not be expected to produce skin trauma. Thus, the use of these materials or other compounds interfering with an assay that do not cause skin trauma might go unnoticed by the technician removing the patch if the fluid contents of the material have had time to evaporate across the outer layer of the patch. However, "Visine" and most other adulterants would be expected to contain ionic materials.

Thus, in order to detect the use of an adulterant, test strips can be incorporated into the patch which will detect the presence of various ionic materials or of extremes of pH. Litmus paper, such as Hydrion pH test paper, available from Baxter Scientific Products, is well known as an indicator of variances of pH. Accordingly, a short piece, for example 1 cm by ½ cm, of litmus paper could be incorporated into the patch to detect the various household products identified above which are known to be highly acidic or basic.

Many test strips are also known for detecting the presence of ionic materials. For example Baxter Scientific Products supplies test strips from a variety of manufacturers for the detection of each of the following ions: aluminum, ammonium, chromate, cobalt, copper, ion, nickel, nitrate, peroxide, sulphite, tin, and calcium. In addition, test strips sold under the name "Qantab" are available from Baxter Scientific Products which identify the presence of chlorine ions. Other test strips available from the same supplier show glucose, protein, and ketones. Most of these test strips are read by simply comparing the color of the strips with a color chart included with the strips. Thus, the test strips provide a simple method of identifying the introduction of any of a variety of adulterant materials.

In order to detect adulterants, such as "Visine," which contain ionic materials not known to the person performing the test, the tester must first assay the adulterant using a variety of test strips for ions to ascertain which ions are present in the materials. Once the appropriate ions are detected, the test strips corresponding to those ions can be incorporated into the patch in order to provide an indication that the adulterant has been added to the patch.

Curiously, any particular adulterant might produce false negative results in some assays and false positive results in others. For each assay, the common adulterants which could be used to produce false negative results could be identified by testing the assays with the addition of small amounts of these known materials. Test strips could then be included which would detect the addition of these adulterants.

In a preferred embodiment, the test strip or strips are placed facing the skin, where the strips are not visible to the wearer. The wearer is thereby not provided any feedback which aids the wearer in deception.

E. Use of a Light Attenuation Layer to Prevent Tampering

Many biological compounds are known to be affected by various spectral bands of light energy. For example, urine samples for analysis of LSD must be kept from exposure to strong light. (Schwartz, *Arch. Inter. Med.* 148: 2407–12 (1988)). Further examples of compounds which require protection from light include cocaine hydrochloride (*Martindale Extra Pharmacopoeia*, 29th Ed., p. 1213) and morphine sulphate (Id., p. 1310). It is expected that these and other compounds may be affected by exposure to light while being concentrated in the collection patch as well.

Many analytes to be determined by a patch of the present invention may require collection and storage in the patch for prolonged periods of time (up to several weeks). These analytes are, therefore, exposed to substantial quantities of photoradiation. This quantity of photoradiation may be substantially greater than during a urine assay for the same or similar analyte. Also, many analytes have peculiarly high sensitivity to light. Thus, for analytes of peculiarly high photosensitivity or for those requiring prolonged collection and storage, it is particularly important to shield photosensitive analytes from light during prolonged storage in the patch.

Accordingly, in still another embodiment of the present invention, illustrated in FIG. 10, there is provided a test patch 90 having a light attenuation layer 92 between the outer adhesive layer 65 and the concentration zone 14. In FIG. 10, the adhesive layer 65, is shown having stress razors 66, however, this feature is to be understood as being optional in this embodiment of the invention.

The attenuation layer 92 is provided in order to attenuate the transmission of light into the concentration zone 14 where the biological compound of interest is being collected and stored. The layer 92 should be substantially impervious to the transmission of photoradiation, yet should also allow relatively unrestricted passage of the aqueous components of sweat to the outer adhesive layer 65. The layer 92 should be of sufficient porosity that diffusion of the aqueous components of sweat occurs at least as rapidly as sweat normally accumulates in the patch.

Because light of many wavelengths is capable of degrading the various biological compounds which may be of interest, the layer 92 should have optical properties which attenuate light throughout a wide spectrum. Attenuation can be achieved by either reflection or absorption of incoming light. Reflection may be achieved through, for example, the use of any of a variety of metallic surfaces. When used in accordance with certain preferred embodiments of the present invention, the attenuation layer 92 should allow passage of aqueous components of sweat. In order to provide a reflective layer with the suitable permeability, thin metallic foil with small holes can be provided. For example, aluminum foil, commercially available from many sources including Reynolds Aluminum Co., could be perforated with a plurality of small holes.

Absorptive attenuation layers can be provided through the use of a black surface. Preferably, these surfaces would continue to allow permeability of aqueous components of sweat. It is important that any dye or pigmentation in the attenuation layer 92 not bleed when exposed to the aqueous components of sweat and also that it not interfere with any binding chemistry or in the analysis of the analyte. Any of a variety of thin black papers having these properties are commercially available and are suitable for use as in the attenuation layer. For example, black Deltaware cellulose membrane filters available from Baxter Scientific Products have been found to be especially useful for use as an attenuation layer. This product is available in a variety of porosities; more open pores are preferred. Thus, in the preferred embodiment, 0.6 micron black Deltaware filters are provided.

In an alternative to the provision of an attenuation layer (not shown), the adhesive layer 65 can be made to attenuate light, either through absorption or reflection. As an example of an absorptive adhesive layer, black colorant, such as fine carbon black powder, could be incorporated into the extrusion of the adhesive sheet.

VII. Determining Allergic Sensitivity with a Dermal Patch

A. Dermal Allergic Reactions

In a further aspect of the present invention, a patch can be used to determine whether a subject is allergic to a particular allergen. Allergens include various forms of pollen, dust, animal skin and fur, chemicals such as insecticides or food additives, and foods. The presence of an allergen on the skin of an individual sensitive to that allergen causes an immune system reaction, known as an allergic reaction, in that individual.

Certain components of the immune system involved in provoking an allergic reaction, such as IgE, complement, and various immune cells, are believed to be able to migrate in the dermis. Components of the immune system also circulate in the blood supplying the skin, and as part of an allergic reaction to an allergen on the skin the permeability of the blood vessels supplying the skin is increased. Immune components of the blood are thereby also believed to participate in a dermal allergic reaction. Thus, the presence of an allergen on the skin results in the migration and concentration of immune components of the body on the surface of the skin where the allergen is present.

B. Using Dermal Patches to Determine Alergic Sensitivity

A subject, preferably a mammal, can be tested for its sensitivity to an allergen by contacting an allergen to the skin of the subject and then detecting any immune components which pass through the skin of the subject and onto a patch of the present invention. In this embodiment, a patch is used which contains an allergen in fluid communication with the skin of the subject when the patch is worn on the skin of the subject. For example, the allergen can be contained in the absorbent material of the patch.

In a preferred embodiment, an agent is also present in the patch in fluid communication with the skin of a wearer of the patch. The agent is one capable of increasing the permeability of the capillaries in the subject's dermis. Such an agent can thus increase the permeability of the capillaries in the dermis beneath the patch and facilitate the flow of immune components to the site of the allergen.

To determine whether a subject is allergic to a particular allergen, a patch of the present invention which additionally includes an allergen is placed on the surface of the skin of the subject. In this embodiment, when perspiration reaches the patch, the allergen is in fluid communication with the skin of the subject and contacts the skin so as to cause an allergic reaction in the subject, if the subject is sensitive to the allergen. The patch will then be able to collect bodily components on the absorbent material of the patch which are associated with an allergic reaction, such as immune system components, which migrate to the location of the allergen. Once such components have accumulated in the absorbent material, the patch is removed, and the presence of such components is detected. If such allergic reaction-associated components are present on the patch, this is indicative that the subject is allergic to the allergen tested.

Alternatively, the skin of the subject can be exposed to an allergen in any other way, such as simply by placing a sample of the allergen on the skin of the subject. Perspiration and other components expressed through the skin can then be accumulated in a patch of the present invention located proximate to the area of the skin of the subject which was exposed to the allergen. If an analyte indicative of an allergic reaction is then detected in the perspiration accumulated on the patch, the subject can be diagnosed as being allergic to the allergen.

The patch used in this embodiment of the present invention can be any of the types previously described. Preferably, a specific binding partner capable of binding and concentrating particular bodily components indicative of an allergic reaction are included in the absorptive layer (or concentration zone) of this aspect of the present invention.

As an example of the present embodiment of the invention, an antigen such as pollen can be placed in the absorptive layer of the patch so that when perspiration penetrates the absorptive layer and brings moisture to that layer, the allergen can migrate through the absorptive layer to the lower surface of the patch in contact with the skin and provoke an allergic reaction, if the subject is prone to develop an allergic reaction to the allergen. Alternatively, the allergen can be placed directly on the lower surface of the patch so that it immediately comes into contact with the skin of a subject wearing the patch.

After an immune response is triggered in a subject who is allergic to the allergen, components involved in the response will increase in concentration in the vicinity of the patch, since it is the site of the allergen. As sensible and insensible perspiration pass through the skin and into the patch, the immune components which pass through the skin with such perspiration concentrate on the absorptive layer of the patch.

Agents which increase capillary permeability in the dermis immediately beneath the patch are preferably included in the patch. Molecules circulating in the capillaries beneath the skin can thereby be made to diffuse into the interstitial space of the skin and from there into perspiration. Such perspiration can then carry these molecules into the patch so that they can be detected.

The following examples describe only specific applications of the present invention.

EXAMPLE 1

Preparation of Monoclonal Antibodies to CK-MB for Use on a Test Patch

In accordance with one known process for preparing monoclonal antibodies, mice such as Balb/c female mice or other mouse strains or even other suitable animals such as rats or rabbits are immunized with an amount of the CK-MB enzyme to initiate an immune response. The enzyme dosage and immunization schedule for producing useful quantities of suitable splenocytes can be readily determined depending on the animal strain used.

The size and spacing of doses of CK-MB or other antigen are of prime importance in the antibody response. Fortunately, a wide range of antigen doses commonly affords immunity against harmful agents. Thus, a small dose of antigen is usually sufficient to initiate an antibody response, i.e., microgram quantities of proteins are frequently adequate. However, a minimum dosage for initiating an immune response does typically exist, although doses of antigen below the minimum dose necessary to initiate an antibody response will usually maintain antibody production which is already in process. For example, an initial immunization with approximately 50 $\mu$g of the enzyme may be followed by a hyperimmunization series of five injections.

When certain compounds which are themselves not necessarily antigenic are mixed with an antigen, enhanced antibody production against the antigen occurs, as evidenced by the appearance of large amounts of antibody in the serum, a prolonged period of antibody production, and a response to lower doses of antigen. Such substances are called "adjuvants" and include Freund's incomplete and complete adjuvants and alum gels. Thus, a given dose of antigen is usually more effective when injected subcutaneously with an adjuvant or when injected as repeated small aliquots than when administered intravenously.

Typically, the adjuvants of Freund are preferred. The original "complete" Freund's adjuvant mixture consists of mineral oil, waxes and killed tubercle bacilli. Antigen is added to the adjuvant mixture in an aqueous phase to form a water-in-oil emulsion in which each water droplet is surrounded by a continuous oil phase containing tubercle bacilli. The mixture is commonly injected subcutaneously into experimental animals. Injection stimulates a marked granulomatous reaction with lesions consisting largely of collections of histiocytes, epithelioid cells and lymphocytes. The local lymph node shows a small increase in plasma cells.

Following the immunization with a primary dose of a soluble protein antigen, specific antibodies normally first appear in the serum after a few days and then increase in number until about the second week. Thereafter, the number of serum antibodies slowly declines over a period of weeks to months.

The first serum antibodies to appear after antigenization are IgM antibodies. These are usually followed by the appearance of IgG antibodies. Later, as antibody serum levels increase, IgM antibodies disappear, probably as a result of specific feedback suppression of IgG antibodies.

After the "primary response" to a protein has passed, a second dose of the same antigen given months or even years later usually elicits an intense and accelerated "specific secondary response" in which serum antibody usually begins to rise within two or three days of exposure. The serum levels of antibody in a secondary response may reach as high as 10 mg per ml.

The animal is subsequently sacrificed and cells taken from its spleen are suspended in an appropriate medium and fused with myeloma cells, such as those obtainable from the murine cell line Sp2/O-Ag14. The result is hybrid cells, referred to as "hybridomas," which are capable of reproduction in vitro and which produce a mixture of antibodies specific to each of the various recognizable sites on the CK-MB enzyme.

The myeloma cell line selected should be compatible with the spleen cells, and optimally should be a cell line of the same species as the spleen cells. Although the murine cell line Sp2/O-Ag14 has been found to be effective for use with mouse spleen cells, other myeloma cell lines can alternatively be used. See, for example, *Nature*, 276: 269-270 (1978).

The myeloma cell line used should preferably be of the so-called "drug resistant" type, so that any unfused myeloma cells will not survive in a selective medium, while hybrid cells will survive. A variety of drug resistant myelomas are known.

The mixture of unfused spleen cells, unfused myeloma cells and fused cells are diluted and cultured in a selective medium which will not support the growth of the unfused myeloma cells for a time sufficient to allow death of all unfused cells. A drug resistant unfused myeloma cell line will not survive more than a few days in a selective medium such as HAT (hypoxanthine, aminopterin and thymidine). Hence, the unfused myeloma cells perish. Since the unfused spleen cells are nonmalignant, they have only a finite number of generations until they fail to reproduce. The fused cells, on the other hand, continue to reproduce because they possess the malignant quality contributed by the myeloma parent and the enzyme necessary to survive in the selected medium contributed by the spleen cell parent.

The supernatant from each of a plurality of hybridoma containing wells is evaluated for the presence of antibody to a specific site unique to the CK-MB enzyme structure. Hybridomas are then selected producing the desired antibody to that specific site. This selection may be, for example, by limiting dilution, in which the volume of diluent is statistically calculated to isolate a certain number of cells (e.g., 1 to 4) in each separate well of a microliter plate. In this way, individual hybridomas may be isolated for further cloning.

Once the desired hybridoma has been selected, it can be injected into host animals of the same species as those used to prepare the hybridoma, preferably syngeneic or semi-syngeneic animals. Injection of the hybridoma will result in the formation of antibody producing tumors in the host after a suitable incubation time, resulting in a very high concentration of the desired antibody in the blood stream and in the peritoneal exudate of the host. Although the hosts have normal antibodies in their blood and exudate, the concentration of these normal antibodies is only about 5% of the concentration of the desired monoclonal antibody. The monoclonal antibody may then be isolated in accordance with techniques known in the art.

EXAMPLE 2

Preparation of Microbead Test Patch

One specific application of the present invention is the dual determination of skeletal muscle and cardiac muscle status as a result of exercise. A dermal patch is constructed in accordance with the embodiment illustrated at FIGS. 3 and 3a. The gauze layer is prepared by cutting a circular patch having an approximately 1-inch diameter from a Johnson & Johnson non-stick gauze pad. The inner and outer porous layers are next prepared by cutting two circular patches of Ultipor (nylon 6), from Pall Corporation in Glen Cove, N.Y. Ultipor membrane is both fluid permeable and microporous, and a membrane is selected having, for example, a 1 micron rating. The microbead layer is prepared by covalently bonding monoclonal antibody raised against CK-MB to a multiplicity of polystyrene beads having a mean particle size of at least about 10 microns.

The patch is assembled by distributing approximately 0.2 gram of microbeads across the surface of one of the porous layers. The second porous layer is thereafter disposed adjacent the microbeads, and the gauze layer is next placed on top of the second porous layer. At this point, the patch is upside-down. The peripheral edges of each of the first and second porous layers and the gauze layers are secured together by conventional heat-sealing techniques. Thereafter, the subassembly is turned over and an annular torus of adhesive tape having approximately a 2-inch outside diameter and slightly less than a 1-inch inside diameter is secured thereto to produce a finished patch.

EXAMPLE 3

Cardiac Muscle Status Test

The patch of Example 1 is then secured to the chest of a healthy 40-year old male and worn throughout a 36-mile (130-minute) bicycle ride. Upon removal of the patch following the ride, the test patch is immersed in a first solution containing an excess of enzyme labeled anti-CK-MB for approximately 30 minutes, to permit conjugation of labeled antibody with immobilized analyte. The patch is then rinsed under tap water to remove unbound labeled antibody and immersed in a second solution containing a substrate for the bound enzyme label, which undergoes a color change when acted upon by the enzyme. Appearance of color through the top porous layer indicates the presence of CK-MB, and possible cardiac injury. Comparison to a color chart permits rough quantification.

EXAMPLE 4

Test for Use of Marijuana

THC polyclonal antibody from sheep (available from Biogenesis, Bournmouth, England) is diluted 1:100 in PBS (pH 7.5). The antibodies are bound to Gelman $0.45\mu$ (SU-450) Ultrabind Supported Membrane, following the protocol in Gelman Original Equipment Manufacturer application P.N. 31,084. The membranes are air dried. Disks, $\frac{3}{8}$ inch in diameter, are cut from the coated Gelman membranes. These $\frac{3}{8}$ inch disks are mounted at the center of a $\frac{1}{4}$ inch diameter hole cut in the center of a one inch diameter circle of Tegaderm 1625 Transparent Dressing (available from Minnesota Mining and Manufacturing, St. Paul, Minn.).

Three mounted membranes are secured to the chest of a subject who then smokes a marijuana cigarette. Three mounted membranes are also secured to a subject who has never used marijuana in any form and who agrees not to use it for the next seven days. The membranes remain in place until they are removed, seven days later. Each of the removed membranes is flushed five times with 300 $\mu$l of 0.2% Tween 20 in PBS. The membranes are incubated for 30 minutes in 100 $\mu$l of E-Z Screen Cannabinoid enzyme conjugate from the E-Z Screen Test Kit (available from Environmental Diagnostics, Inc., Burlington, N.C.).

After incubation, each membrane is flushed three times with 300 $\mu$l of 0.2% Tween 20 in PBS, followed by three flushes with PBS alone. The membranes are then incubated in TMB Membrane Peroxide Substrate (available from Kirkegaard & Perry Labs, Gaithersburg, Md.) for 10 minutes. A light blue background appears in all six membranes. White dots appear over the background on the three membranes taken from the subject who smoked a marijuana cigarette, indicating sweat gland output of sweat containing THC derivatives. No white dots appear on the three membranes taken from the subject who has never used marijuana.

EXAMPLE 5

Positive Control Patch

Mouse anti-human IgG, Fc monoclonal antibody (available from ICN, Costa Mesa, Calif.) is diluted 1:100 in PBS (pH 7.5). The antibodies are bound to Gelman $0.45\mu$ (SU-450) Ultrabind Supported Membrane, following the protocol in Gelman Original Equipment Manufacturer application P.N. 31,084. The membranes are air dried. Disks, $\frac{3}{8}$ inch in diameter, are cut from the coated Gelman membranes. These $\frac{3}{8}$ inch disks are centered and mounted on a $\frac{1}{4}$ inch diameter hole cut in the center of a one inch diameter circle of Tegaderm 1625 Transparent Dressing.

Three mounted membranes are secured to the chest of five human subjects. The membranes remain in place until they are removed, seven days later. Each of the removed membranes is flushed five times with 300 $\mu$l of 0.2% Tween 20 in PBS. The membranes are incubated for 30 minutes in 100 $\mu$l of Horseradish peroxidase enzyme conjugated to goat anti-human IgG, Fc polyclonal antibody (available from ICN, Costa Mesa, Calif.) diluted 1:1000 in PBS.

After incubation, each membrane is flushed three times with 300 $\mu$l of 0.2% Tween 20 in PBS, followed by three flushes with PBS alone. The membranes are then incubated in TMB Membrane Peroxide Substrate (available from Kirkegaard & Perry Labs, Gaithersburg, Md.) for 10 minutes. Blue dots corresponding to individual sweat ducts appear over the background on all of the membranes, indicating that the chemistry of the patches is operative by their detection of the IgG expected in the sweat of all subjects.

EXAMPLE 6

Chemical Modification of Cocaine Collected on a Patch

Absorption disks, $\frac{3}{8}$ inch in diameter, are cut from Gelman membranes (Gelman $0.45\mu$ (SU-450) Ultrabind Supported Membranes). These $\frac{3}{8}$ inch disks are mounted at the center of a $\frac{1}{4}$ inch diameter hole cut in the center of a one inch diameter circle of Tegaderm 1625 Transparent Dressing (available from Minnesota Mining and Manufacturing, St. Paul, Minn.) to form a patch.

Three of such patches are secured to the chest of a subject who then ingests cocaine. Three patches are also secured to a subject who has never used cocaine in any form and who agrees not to use it for the next seven days. The patches remain in place until they are removed seven days later from each subject.

The cocaine molecules and other components present in the membranes of each patch are then eluted from the membranes by soaking each of the membranes in a synthetic urine matrix for 30 to 60 minutes at room temperature with mechanical agitation to form an analyte solution. Following elution, the analyte solutions derived from each of the patches are brought to a pH of 11 by the addition of NaOH to each of the solutions. The solutions are reacted for 20 minutes at pH 11 and at room temperature, after which the solutions are neutralized with HCl.

Each solution is then subjected to diagnostic analysis with the Roche RIA system (Nutley, N.J.) for detecting the metabolite of cocaine BE. The subject who ingested cocaine tests positive for the cocaine metabolite BE, while the subject who did not consume cocaine over the test period does not test positive for BE.

EXAMPLE 7

Preparation and Use of a Dissolvable Absorption Disk

Nylon 6/6 fibers (Vydyne 909 from Monsanto Co.) are formed into an absorbent gauze. Disks approximately $\frac{3}{8}$ inch in diameter are cut from such gauze and are then mounted at the center of a $\frac{1}{4}$ inch diameter hole cut in the center of a one inch diameter circle of Tegaderm 1625 Transparent Dressing (available from Minnesota Mining and Manufacturing, St. Paul, Minn.) to form a patch. Such a patch is then applied to a subject.

The subject is directed to ingest cocaine, and a quantity of perspiration is then allowed to accumulate on the patch.

When a sufficient period of time has passed for a detectable amount of cocaine to accumulate on the patch, the patch is removed from the subject and placed in an insoluble container. A base capable of dissolving the Nylon 6/6 fibers is then poured over the patch. Once the nylon absorption disk is dissolved, the undissolved components of the patch are removed from the container. Since cocaine is converted into benzoylecgonine (BE) in the presence of a base, the cocaine contained in the disk is metabolized to BE when the disk is dissolved.

The solution of the dissolved nylon, BE, and the other remaining components of the used absorption disk are next neutralized. This solution is then analyzed using a Roche RIA system (Nutley, N.J.). The BE in the solution is detected and the amount of BE concentrated in the absorption disk is determined.

EXAMPLE 8

Quantitative Determination of a Component of Perspiration

To determine how much of an analyte is contained in a given volume of sweat, a patch is first constructed having a support layer made from a polyester-supported polycarbonate microporous membrane, manufactured by Nuclepore (Menlo Park, Calif.). Over this is placed an absorbent material such as Filtration Sciences medical grade paper (FS#39) for accumulating and concentrating perspiration. The surface area of the layer of absorbent material should be the same as or smaller than that of the support layer so that when placed on a subject's skin, only the support layer is in contact with the subject's skin. Over this layer is then placed an outer protective layer made of 1625 Tegaderm wound dressing made by the 3M Company (St. Paul, Minn.). This outer layer is of a larger surface area than either the support layer or the absorbent material and covers both of these layers. The outer layer separates the absorbent material from the outside of the patch and helps prevent perspiration from entering the absorbent layer except through the support layer. The outer perimeter of the outer layer has an adhesive on the side of the outer layer that faces the skin of a subject when the patch is applied to the skin of such a subject in order to secure the patch.

Such a patch is next placed on the skin of a subject whose perspiration is to be tested for the presence of theophylline. The subject wears the patch for 7 days, during which time perspiration passes through the support layer at a rate of less than 6 grams/m²/hour. After this the patch is removed and subjected to analysis to determine the amount of theophylline contained in the patch.

To determine the volume of sweat that has passed into the absorbent material of the patch, the rate at which perspiration passed into the absorbent material is multiplied by the amount of time the patch was worn, i.e., 7 days. The amount of theophylline contained in the patch is then determined. These numbers are then related in order to determine the amount of analyte contained in a given volume of perspiration by dividing the amount of the analyte in the patch by the volume of perspiration which passed through the support layer into the absorbent material.

EXAMPLE 9

Preparation and Use of a Dermal Patch to Determine the Sensitivity of a Subject to an Allergen In order to determine whether an individual is allergic to cat hair, a preparation containing cat hair is first placed on the lower surface of a disk ⅜ inch in diameter made of Filtration Sciences medical grade paper (FS#39). The upper surface of the disk is mounted at the center of a ¼ inch diameter hole cut in the center of a one inch diameter circle of Tegaderm 1625 Transparent Dressing (available from Minnesota Mining and Manufacturing, St. Paul, Minn.). The patch is then placed on the surface of the skin of a human subject for approximately 3 days in order to accumulate perspiration on the disk and form a concentrate. The disk is then removed and analyzed to detect IgA against cat hair. The presence of IgA against cat hair indicates that the subject has expressed an allergic reaction to the cat hair antigen.

Although this invention has been described in terms of certain preferred embodiments and assay schemes, other embodiments and assays that are apparent to those of ordinary skill in the art are also within the scope of this invention. Accordingly, the scope of the invention is intended to be defined only by reference to the appended claims.

What is claimed is:

1. A system for determining the presence of an analyte in perspiration of a subject mammal comprising:
   a) a dermal patch to be worn on the skin of a subject mammal, said patch comprising:
      i) an absorbent material for collecting components of perspiration which diffuse through the skin of said subject, said absorbent material having a first and second side, said first side of said absorbent material being adapted to be in fluid communication with the skin of said subject, wherein said absorbent material comprises a material which can be dissolved into a solution with a solvent such that said solvent and the dissolved absorbent material in solution do not interfere with the analysis of said components of perspiration; and
      ii) adhesive on said patch for removably securing said first side of said absorbent material in fluid communication with the skin of said subject; and
   b) a solvent which can dissolve said absorbent material of said dermal patch into solution, wherein said solvent does not interfere with the analysis of said components of perspiration.

2. The system of claim 1, wherein said patch additionally comprises a fluid permeable support layer adjacent said first side of said absorbent material in fluid communication with said subject's skin when said patch is worn on said subject's skin, wherein said support layer comprises a rate-limited structure that limits the rate of diffusion of perspiration through said support layer, said support layer being located between said absorbent material and the subject's skin when said patch is on the subject's skin.

3. The system of claim 1, wherein said absorbent material is selected from the group consisting of protein, nylon 6/6, phenolic, polyurethane (TP), and polyester (PBT), and said solvent is selected from the group consisting of an acid and a base.

4. The system of claim 1, wherein said absorbent material is polystyrene and said solvent is selected from the group consisting of chlorinated hydrocarbons, aromatic hydrocarbons, esters, ketones, essential oils of high terpene content, and turpentine.

5. The system of claim 4, wherein said solvent is selected from the group consisting of cyclohexanone, dichloroethylene, and methylenedichloride.

6. The system of claim 1, additionally comprising a gas permeable outer protective layer, said outer protective layer having a first and second side, wherein said first side of said outer protective layer is adjacent said second side of said absorbent material, and wherein said adhesive is located on said first side of said outer protective layer.

7. The system of claim 6, wherein said patch further comprises a pooling area between said outer protective layer and the skin of said subject when said patch is on said subject's skin and a fluid, said absorbent material being in fluid communication with said pooling area only through said fluid permeable support layer, said fluid permeable support layer being adjacent said first side of said absorbent material in fluid communication with said subject's skin when said patch is worn on said subject's skin.

8. The system of claim 1, wherein said absorbent material is provided with a specific binding partner for an analyte present in the perspiration of said subject.

9. The system of claim 1, wherein said absorbent material contains a component of said perspiration of said subject, and wherein said component is a drug of abuse.

10. The system of claim 9, wherein said drug of abuse is cocaine.

11. The system of claim 2, wherein said rate-limited structure of said support layer allows the passage of perspiration through said support layer at a rate lower than the insensible rate of perspiration through the skin of said subject.

12. A method of detecting metabolites of an analyte contained in perspiration of a subject mammal, wherein said analyte appears in a chemically modified form in a body fluid of said subject other than perspiration, comprising:
 a) passing said analyte through the skin of said mammal in the perspiration of said mammal;
 b) collecting said analyte on a dermal patch worn on the skin of said subject mammal, said patch comprising:
  i) an absorbent material for collecting components of perspiration which diffuse through the skin of said subject, said absorbent material having a first and second side, said first side of said absorbent material being adapted to be in fluid communication with the skin of said subject; and
  ii) adhesive on said patch for removably securing said first side of said absorbent material in fluid communication with the skin of said subject;
 c) chemically modifying said analyte after said analyte has been collected on said absorbent material in order to convert said analyte into the chemically modified form of said analyte which appears in said body fluid of said subject other than perspiration; and
 d) detecting said chemically modified form of said analyte.

13. The method of claim 12, additionally comprising the step of freeing said analyte from said absorbent material after said analyte has been collected on said absorbent material.

14. The method of claim 13, wherein the freeing step comprises eluting said analyte from said absorbent material with a solvent.

15. The method of claim 13, wherein said absorbent material is dissolvable by said solvent into a solution such that the dissolved material and solution do not interfere with the detection of said analyte, and said freeing step involves dissolving said absorbent material and thereby eluting said analyte.

16. The method of claim 12, wherein said step of chemically modifying comprises exposing said analyte to a solution having an alkaline pH.

17. The method of claim 12, further comprising heating said analyte during said step of chemically modifying.

18. The method of claim 12, wherein said analyte is cocaine.

19. The method of claim 12, wherein said step of chemically modifying comprises incubating said analyte with an enzyme capable of hydrolyzing said analyte.

20. The method of claim 12, wherein said step of chemically modifying said analyte comprises reacting said analyte with a cholinesterase enzyme.

21. The method of claim 12, wherein said step of chemically modifying said analyte comprises converting said analyte into a form of said analyte which appears in the urine of said subject.

22. The method of claim 12, wherein said step of chemically modifying said analyte comprises converting said analyte into a form of said analyte which appears in the blood of said subject.

23. The method of claim 12, additionally comprising the step of concentrating said analyte on said dermal patch after collecting perspiration containing said analyte on said patch, wherein said perspiration collects in said absorbent material of said patch, and wherein said concentrating step is performed by passing water from said perspiration in said absorbent material through a gas permeable outer protective layer, said outer protective layer having a first and second side, wherein said first side of said outer protective layer is adjacent said second side of said absorbent material, and wherein said adhesive is located on said first side of said outer protective layer.

24. A method for determining the presence of an analyte in perspiration of a subject mammal, comprising the steps of:
 a) placing a dermal patch on the skin of said subject, said patch comprising:
  i) an absorbent material for collecting components of perspiration which diffuse through the skin of said subject, said absorbent material having a first and second side, said first side of said absorbent material being adapted to be in fluid communication with the skin of said subject, wherein said absorbent material comprises a material which can be dissolved such that the dissolved absorbent material does not interfere with the analysis of said components of perspiration; and
  ii) adhesive on said patch for removably securing said first side of said absorbent material in fluid communication with the skin of said subject;
 b) accumulating perspiration containing said analyte from said subject on said patch;
 c) dissolving said absorbent material of said patch containing said analyte into a solution, wherein said solution does not interfere with the analysis of said components of perspiration; and d) detecting said analyte in said solution.

25. The method of claim 24, wherein said detecting step additionally comprises chemically modifying said analyte and detecting a metabolite of said analyte in order to detect the presence of said analyte.

26. The method of claim 24, wherein said absorbent material is selected from the group consisting of protein, nylon 6/6, phenolic, polyurethane (TP), and polyester (PBT), and wherein said dissolving step comprises contacting said absorbent material with a solvent, said solvent being selected from the group consisting of an acid and a base.

27. The method of claim 24, wherein said absorbent material is polystyrene and wherein said dissolving step comprises contacting said absorbent material with a solvent, said solvent being selected from the group consisting of chlorinated hydrocarbons, aromatic hydrocarbons, esters, ketones, essential oils of high terpene content, and turpentine.

28. The method of claim 27, wherein said solvent is selected from the group consisting of cyclohexanone, dichloroethylene, and methylenedichloride.

29. The method of claim 24, additionally comprising the step of concentrating said analyte on said dermal patch after accumulating perspiration containing said analyte on said patch, wherein said perspiration accumulates in said absorbent material of said patch, and wherein said concentrating step is performed by passing water from said perspiration in said absorbent material through a gas permeable outer protective layer, said outer protective layer having a first and second side, wherein said first side of said outer protective layer is adjacent said second side of said absorbent material, and wherein said adhesive is located on said first side of said outer protective layer.

* * * * *

UNITED STATES PATENT AND TRADEMARK OFFICE
CERTIFICATE OF CORRECTION

PATENT NO. : 5,441,048
DATED : August 15, 1995
INVENTOR(S) : Donald W. Schoendorfer It is certified that error appears in the above-indentified patent and that said Letters Patent is hereby corrected as shown below:

Column 31, Line 22, please change "Alergic" to --Allergic--.

Column 39, Line 19, after "and a fluid", please insert --permeable support layer--.

Signed and Sealed this

Thirteenth Day of February, 1996

Attest:

BRUCE LEHMAN

*Attesting Officer*     *Commissioner of Patents and Trademarks*